(12) United States Patent
Kuramori et al.

(10) Patent No.: US 7,693,572 B2
(45) Date of Patent: Apr. 6, 2010

(54) WORKABILITY EVALUATING APPARATUS, WORKABILITY EVALUATING METHOD, AND WORKABILITY EVALUATING PROGRAM

(75) Inventors: Akira Kuramori, Kanagawa (JP);
Noritaka Koguchi, Kanagawa (JP);
Tsugutake Sadoyama, Ibaraki (JP);
Masayoshi Kamijo, Nagano (JP)

(73) Assignee: The Yokohama Rubber Co., Ltd., Tokyo (JP)

( * ) Notice: Subject to any disclaimer, the term of this patent is extended or adjusted under 35 U.S.C. 154(b) by 1246 days.

(21) Appl. No.: 11/219,773

(22) Filed: Sep. 7, 2005

(65) Prior Publication Data

US 2006/0073894 A1  Apr. 6, 2006

(30) Foreign Application Priority Data

Sep. 7, 2004   (JP) .............................. 2004-259675

(51) Int. Cl.
*A61B 5/04* (2006.01)
*A61B 5/00* (2006.01)
*A61B 5/05* (2006.01)
*A61B 5/103* (2006.01)
*A61B 5/117* (2006.01)

(52) U.S. Cl. ........................ 600/546; 600/300; 600/301; 600/306; 600/372; 600/382; 600/384; 600/547; 600/587; 600/595

(58) Field of Classification Search ................. 600/300, 600/301, 306, 372, 382, 384, 546, 547, 587, 600/595
See application file for complete search history.

(56) References Cited

U.S. PATENT DOCUMENTS

2005/0277843 A1    12/2005    Kuramori et al.

FOREIGN PATENT DOCUMENTS

| JP | 2002-225585 | 8/2002 |
| JP | 2003-177079 A | 6/2003 |
| WO | WO 2004/008957 A1 | 1/2004 |

OTHER PUBLICATIONS

G. E. Loeb et al., "Cross-Correlation of EMG Reveals Widespread Synchronization of Motor Units During Some Slow Movements in Intact Cats," Journal of Neuroscience Methods, vol. 21, (1987) pp. 239-249.

*Primary Examiner*—Max Hindenburg
*Assistant Examiner*—Jeffrey G Hoekstra
(74) *Attorney, Agent, or Firm*—Finnegan, Henderson, Farabow, Garrett & Dunner, L.L.P.

(57) ABSTRACT

A workability evaluating apparatus comprises a myoelectric potential detecting unit, a signal processing unit, an arithmetic operation unit, and an output unit. The myoelectric potential detecting unit detects time-series fluctuations in myoelectric potentials of at least one pair of muscles, which show antagonistic activities while operating equipment among muscles of an operator used to operate the equipment, as myoelectric potential signals. The signal processing unit processes the detected myoelectric potentials. The arithmetic operation unit calculates time-series data of a first correlation coefficient in a specified sampling time between signals obtained by processing the myoelectric potential signals from the pair of antagonistic muscles, and performs evaluation of workability in operating the equipment by using the calculated time-series data. The output unit outputs a result of the performed evaluation.

12 Claims, 18 Drawing Sheets

WORKABILITY EVALUATING APPARATUS, WORKABILITY EVALUATING METHOD, AND WORKABILITY EVALUATING PROGRAM

CROSS-REFERENCE TO RELATED APPLICATION

This application claims the benefit of Japanese Patent Application No. 2004-259675, filed Sep. 7, 2004.

BACKGROUND OF THE INVENTION

The present invention relates to a workability evaluating apparatus, a workability evaluating method, and a workability evaluating program, each of which makes quantitative evaluations of workability, such as the smoothness or comfortability of operating equipment, based on myoelectric potentials.

A human being or an animal bends or stretches limbs or the like by contracting a muscle to thereby perform a desired action. In performing an action, a given muscle contracts and another muscle corresponding thereto relaxes. In other words, a human being or an animal performs an action by antagonizing muscles. The muscle which contracts during an action is termed a prime mover (agonist), while a muscle which relaxes is termed an antagonist.

In the case of steering a steering wheel of a vehicle during driving or operating a control lever of an aircraft during flight, symmetric contraction is caused between the prime mover and the antagonist when an excessive strain results from mental load or a difficult control operation.

As means for instantaneously reflecting such muscle activity, an electromyogram representing a myoelectric potential as time-series data has been used. The electromyogram has been used as optimum bio-information for capturing instantaneous sensory information.

There has been proposed a technology with which load placed on a driver due to a driving operation is determined by using an electromyogram and the result of the determination is used for a vehicle control apparatus for properly setting control conditions for a vehicle (see, e.g., JP 2002-225585 A).

JP 2002-225585 A discloses a process of measuring both of a myoelectric potential at a prime mover and a myoelectric potential at an antagonist, calculating a value (competitive characteristic quantity) associated with the competition between the two myoelectric potentials, and determining the magnitude of a load placed on a driver due to a driving operation, based on the competitive characteristic quantity.

More specifically, the myoelectric potentials at the competitive muscles of the driver are measured by using myoelectric potential sensors, and the competitive characteristic quantity is calculated from the competitive value between the measured myoelectric potentials. When the calculated competitive characteristic quantity exceeds a predetermined threshold, it is determined that the load placed on the driver due to the driving operation has increased (paragraphs [0005] and [0006] in JP 2002-225585 A).

In JP 2002-225585 A, the measurement of the myoelectric potentials is performed by attaching the electrodes of the myoelectric potential sensors (detection sensors) to the surface of the skin. It has been known that, however, when myoelectric potential sensors are attached again after being peeled off, the resistance values between the surface of the skin and the electrodes vary, and therefore it is difficult to maintain the levels of the myoelectric potentials. That is, when the voltage value of the myoelectric potentials is used as an index representing muscle activity in an absolute sense, a determination error may occur occasionally.

SUMMARY OF THE INVENTION

The present invention has been made in view of the above problems and it is therefore an object of the present invention to provide a workability evaluating apparatus and a workability evaluating method, each of which makes quantitative evaluations of workability in operating a device with a high degree of reliability by measuring muscle activity performed by antagonistic movement of a plurality of muscles in a human body during operation of the device. The workability used herein is one index for indicating operability when an operator operates a device, which is represented by smoothness or comfortability of the operation of the device.

According to a first aspect of the present invention, there is provided a workability evaluating apparatus characterized by including: a myoelectric potential detecting unit for detecting time-series fluctuations in myoelectric potentials of at least one pair of muscles, which show antagonistic activities while operating equipment among muscles of an operator used to operate the equipment, as myoelectric potential signals; a signal processing unit for processing the detected myoelectric potentials; an arithmetic operation unit for calculating time-series data of a first correlation coefficient in a specified sampling time between signals obtained by processing the detected myoelectric potential signals from the at least one pair of antagonistic muscles; an evaluation unit for performing evaluation of workability in operating the equipment by using the calculated time-series data of the first correlation coefficient; and an output unit for outputting a result of the evaluation performed by the evaluation unit.

Further, the arithmetic operation unit may calculate plural time-series data of the first correlation coefficients associated with myoelectric potential signals from two or more pairs of antagonistic muscles detected by the myoelectric potential detecting unit, and the evaluation unit may evaluate the workability in operating the equipment by using the plural time-series data of two or more first correlation coefficients obtained from the individual pairs of antagonistic muscles.

Further, according to the present invention, it is preferable that the workability evaluating apparatus further include: an operation-input-quantity detecting unit for detecting an input quantity imparted to an operated portion of the operated equipment and for calculating a basic period of the operation from time-series data of the detected input quantity and determining the length of the sampling time based on the basic period, and that the arithmetic operation unit calculate the time-series data of the first correlation coefficient by using the determined sampling time.

The sampling time preferably ranges from 25% to 100% of the basic period. The input quantity is preferably one of a quantity of displacement of the operated portion and a quantity of angular displacement thereof, or one of a force and a torque that act on the operated portion.

According to a second aspect of the present invention, there is provided a workability evaluating method characterized by including: a myoelectric potential detecting step for detecting time-series fluctuations in myoelectric potentials of at least one pair of muscles, which show antagonistic activities in operating equipment among muscles used to operate the equipment, as myoelectric potential signals; a step of processing the detected myoelectric potentials; an arithmetic operation step for calculating time-series data of a first correlation coefficient in a specified sampling time between signals obtained by processing the myoelectric potential signals from the pair of antagonistic muscles; an evaluation step for performing evaluation of workability in operating the equipment by using the calculated time-series data of the first correlation coefficient; and a step of outputting a result of the evaluation performed in the evaluation step.

Further, the arithmetic operation step may include calculating plural time-series data of the first correlation coefficients associated with myoelectric potential signals from two or more pairs of antagonistic muscles detected in the myoelectric potential detecting step, and the evaluation step may include evaluating the workability in operating the equipment by using the plural time-series data of two or more first correlation coefficients obtained from the individual pairs of muscles.

According to the present invention, it is preferable that the workability evaluating method further include the steps of: detecting an input quantity imparted to an operated portion of the operated equipment; calculating a basic period of the operation from time-series data of the detected input quantity; and determining the sampling time based on the basic period, and that the arithmetic operation step includes calculating the time-series data of the first correlation coefficient by using the sampling time.

The sampling time preferably ranges from 25% to 100% of the basic period. The input quantity is preferably one of a quantity of displacement of the operated portion and a quantity of angular displacement thereof, or one of a force and a torque that act on the operated portion.

According to a third aspect of the present invention, there is provided a program characterized by causing a computer to execute: a step of processing myoelectric potential signals detected as time-series fluctuations in myoelectric potentials of at least one pair of muscles, which show antagonistic activities in operating equipment among muscles used to operate the equipment; an arithmetic operation step for calculating time-series data of a first correlation coefficient in a specified sampling time between signals obtained by processing the myoelectric potentials from the pair of antagonistic muscles; a step for performing evaluation of workability in operating the equipment by using the calculated time-series data of the first correlation coefficient; and a step of outputting a result of the evaluation performed in the evaluation step.

Further, it is preferable that the arithmetic operation step calculate plural time-series data of first correlation coefficients associated with myoelectric potential signals from two or more pairs of antagonistic muscles detected in the myoelectric potential detecting step, and that the evaluation step evaluate the workability in operating the equipment by using the plural time-series data of two or more first correlation coefficients obtained from the individual pairs of muscles.

Further, according to the present invention, it is preferable that the program further includes the steps of: calculating a basic period of the operation from time-series data of an input quantity detected as an input quantity imparted to an operated portion of the operated equipment; and determining the sampling time based on the basic period, and that the arithmetic operation step include calculating the time-series data of the first correlation coefficient by using the sampling time.

The sampling time preferably ranges from 25% to 100% of the basic period. The input quantity is preferably one of a quantity of displacement of the operated portion and a quantity of angular displacement thereof, or one of a force and a torque that act on the operated portion.

The present invention allows for detecting myoelectric potentials at muscles showing antagonistic activities, performing a specified process on signals representing the myoelectric potentials, calculating time-series data of a first correlation coefficient, and evaluating workability by using the time-series data of the first correlation coefficient. By measuring muscle activities during an operation performed antagonistically by a plurality of muscle pairs in a human body, the smoothness of operating equipment can be expressed quantitatively, and the comfortability of the operation can also be expressed.

Accordingly, the present invention can provide an apparatus, a method, and a program which allow quantitative and reliable evaluation of workability in operating a device.

DESCRIPTION OF THE PREFERRED EMBODIMENTS

Referring to the accompanying drawings, an embodiment of a workability evaluating apparatus according to the present invention will be described in detail. In this embodiment, a workability evaluating apparatus 10 is used to evaluate smoothness of an operation during a driving of a vehicle, and myoelectric potentials at deltoid muscles in shoulder portions are measured to evaluate workability.

In general, when a driver driving a vehicle turns the vehicle to the right, for example, the driver grips the wheel mainly with his or her left hand to steer the wheel of the vehicle clockwise, so the deltoid muscle in the left shoulder of the driver contracts, while the deltoid muscle in the right shoulder of the driver relaxes because the right hand of the driver only lightly touches the wheel. The operability (workability) of a wheel steering operation during the driving of a vehicle which is performed by contracting one of the pair of deltoid muscles and relaxing the other as described above can be evaluated by using the workability evaluating apparatus 10 according to the present invention.

Figure 1:
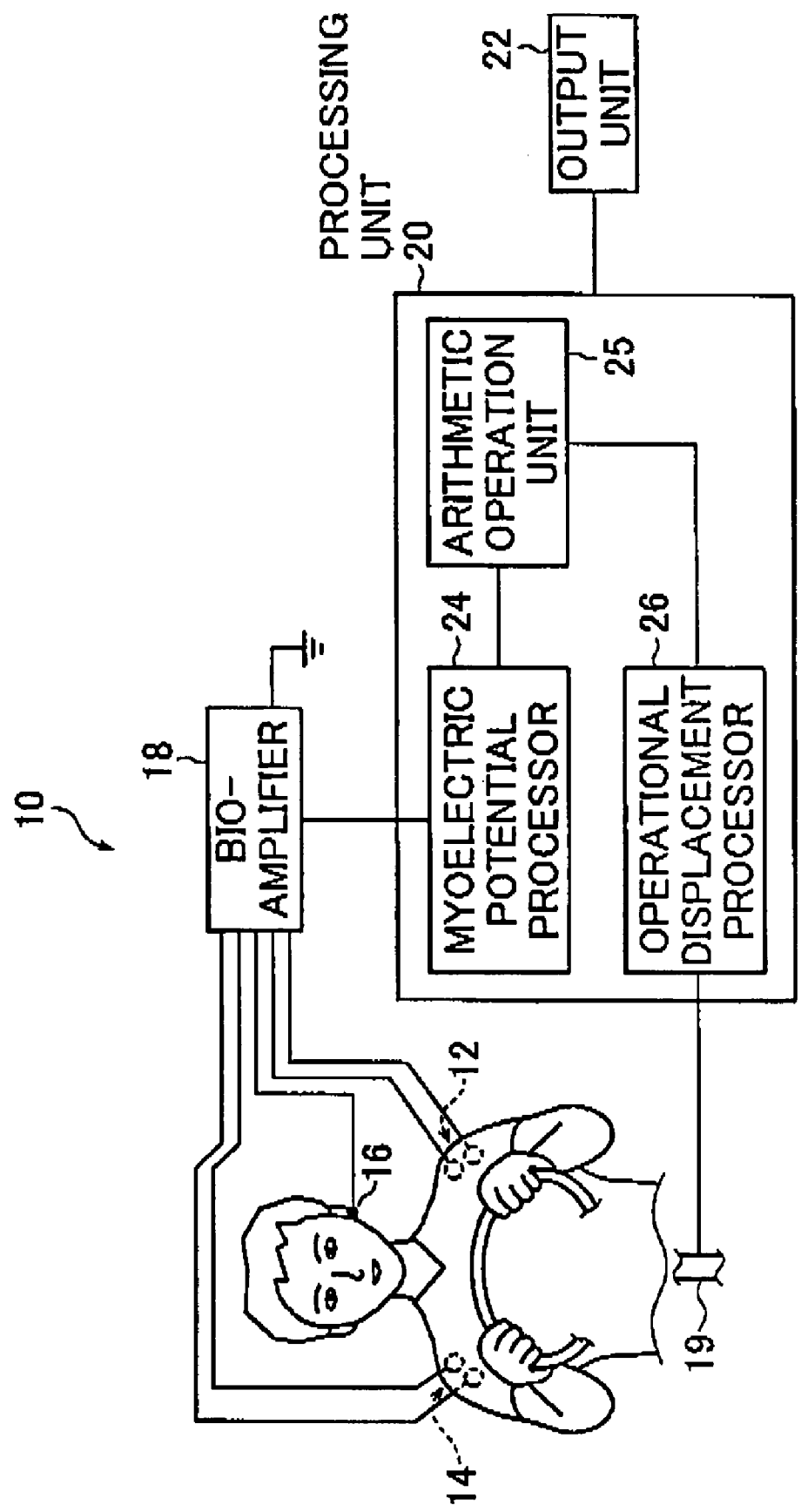
FIG. 1 is a structural view of an example of when a workability evaluating apparatus is used to evaluate operability during a driving of a vehicle.

FIG. 1 is a structural view of the workability evaluating apparatus being used to evaluate operability during the driving of a vehicle. As shown in FIG. 1, the workability evaluating apparatus 10 includes: myoelectric potential sensors 12 and 14 for detecting myoelectric potentials at the left and right deltoid muscles of a driver as a subject under measurement; a ground electrode 16; a bio-amplifier 18 for amplifying myoelectric potentials obtained from the sensors 12 and 14; an operation quantity detector 19 for detecting a displacement of an operated equipment; a processing unit 20 for evaluating workability based on time-series waveforms of the myoelectric potentials detected at the deltoid muscles; and an output unit 22 for displaying the result of the evaluation.

The sensor 12 includes a pair of silver/silver-chloride (Ag/AgCl) plate-like electrodes. The pair of plate-like electrodes are attached to the surface of the skin and are spaced apart by a specified distance of several millimeters.

In this embodiment, in order to detect the myoelectric potentials at the deltoid muscles in the left shoulder of the driver, the plate-like electrodes of the sensor 12 are attached to the surface of the left shoulder, in which the deltoid muscle is located, and are spaced apart by a distance of about 5 millimeters.

The silver/silver-chloride (Ag/AgCl) electrodes are obtained by coating the surface of metal silver with silver chloride, and are particularly effective among reusable general-purpose electrodes in terms of electric properties. However, the electrodes of the sensors 12 and 14 are not limited to the silver/silver-chloride (Ag/AgCl) electrodes and may also be composed of other materials such as stainless steel, carbon, a carbon composite, platinum, gold, silver, titanium, a conductive resin, and a conductive polymer gel.

The myoelectric potential sensor 14 includes a pair of silver/silver-chloride (Ag/AgCl) plate-like electrodes, as in the case of the sensor 12. In order to detect the myoelectric potential at the deltoid muscle in the right shoulder of the driver, the plate-like electrodes of the sensor 14 are attached to the surface of the right shoulder in which the deltoid muscle is located, and are spaced apart by a distance of about 5 millimeters.

Because myoelectric potential signals obtained from the sensors 12 and 14 are extremely weak, the ground electrode 16 is used to remove ambient noise.

Specifically, the removal of the noise is performed in accordance with a bipolar dielectric method by using a pair of electrodes, a ground electrode, and a differential amplifier (pre-amplifier). That is, both a potential difference caused between one electrode of a myoelectric potential sensor and the ground electrode and another potential difference between another electrode and the ground electrode respectively include myoelectric potential signals out-of-phase, while the ambient noise is included in-phase. If the potential differences between the two electrodes are calculated by using the differential amplifier, the noise in-phase is cancelled out, thereby making it possible to obtain only the myoelectric potential out-of-phase.

The ground electrode 16 is connected to the bio-amplifier 18 to be grounded therethrough.

The bio-amplifier 18 is connected to each of the sensors 12 and 14 by using lead lines. Since the myoelectric potentials detected by the sensors 12 and 14 are an extremely low voltage ranging from several microvolts to several millivolts in most cases, the voltage is amplified by the bio-amplifier 18 to an A/D convertible level. The myoelectric potential signals amplified by the bio-amplifier 18 are subjected to A/D conversion and sent as digital signals to the processing unit 20.

The operation quantity detector 19 detects an input quantity (operation quantity) imparted to an operated portion of the operated equipment, such as a displacement, an angular displacement, or an angular torque resulting from a wheel steering operation. According to the type of equipment to be operated, a well-known measuring device such as a steering angle sensor or a displacement gauge can be used.

Specifically, the operation quantity detector 19 detects the steering angle of a steering wheel or the steering torque thereof. Alternatively, the operation quantity detector 19 may also detect the gear level of the AT gear selector of a vehicle or the stepping-on quantity of an accelerator pedal.

The displacement detected by the operation quantity detector 19 is sent to the processing unit 20.

When a periodicity can be observed in the operation based on the operation quantity of the operated equipment, it is preferable that the precision of the evaluation of workability be based on a basic period of the operation, as will be described later.

The processing unit 20 includes: a myoelectric potential processor 24; an operational displacement processor 26; and an arithmetic operation unit 25. The processing unit 20 acquires the myoelectric potential signals amplified by the bio-amplifier 18 and an operational displacement signal detected by the operation quantity detector 19 to evaluate operability in operating the operated equipment. The result of the evaluation is outputted to the output unit 22, such as a display unit, a memory unit, or a control unit.

The processing unit 20 includes: a CPU (Central Processing Unit), which executes processing for various arithmetic operations and collectively controls the individual components; a RAM (Random Access Memory), which functions as a work area for the CPU; a ROM (Read Only Memory), which stores information including a processing program executed by the CPU; and a HDD (Hard Disk Drive), which records therein the processing result of the processing program executed by the CPU, various data, and the like. The CPU, the RAM, and the HDD are connected to one another via buses so that the transmission/reception of various signals can be performed.

The processing unit 20 is connected to each of the bio-amplifier 18, the operation quantity detector 19, and the output unit 22 via an I/O interface.

A method of measuring myoelectric potentials at the deltoid muscles in the shoulder portions will now be described with reference to FIG. 2. The deltoid muscle shown in FIG. 2 is a triangular muscle widely covering the surface of the shoulder portion, and is used to outwardly twist the arm and bend or inwardly turn the shoulder joint.

In the case of measuring the myoelectric potential at the deltoid muscle, the electrodes of the myoelectric potential sensor 14 are attached to a position Y which is away, by the widths of three fingers in a longitudinal direction of the arm, from the outer edge portion X of the clavicle, while being spaced apart by a specified distance. Each of the electrodes of the sensor 14 is attached to the belly of the muscle to be measured in parallel to the muscle fibers.

Before attaching sensor 14 to the surface of the skin, the skin is rubbed off with a scrub to remove contamination, and wiped with alcohol or the like to minimize the resistance between the skin and the electrodes of the sensor. The sensor is then attached to the skin, using an electrode glue. The electric resistance between the skin and the electrodes of the sensor is adjusted to become 30 k$\Omega$ or less in attaching the sensor 14 to the skin. Preferably, the electric resistance in attaching the electrodes to the surface of the skin is adjusted to be 5 k$\Omega$ or less.

Figure 2:
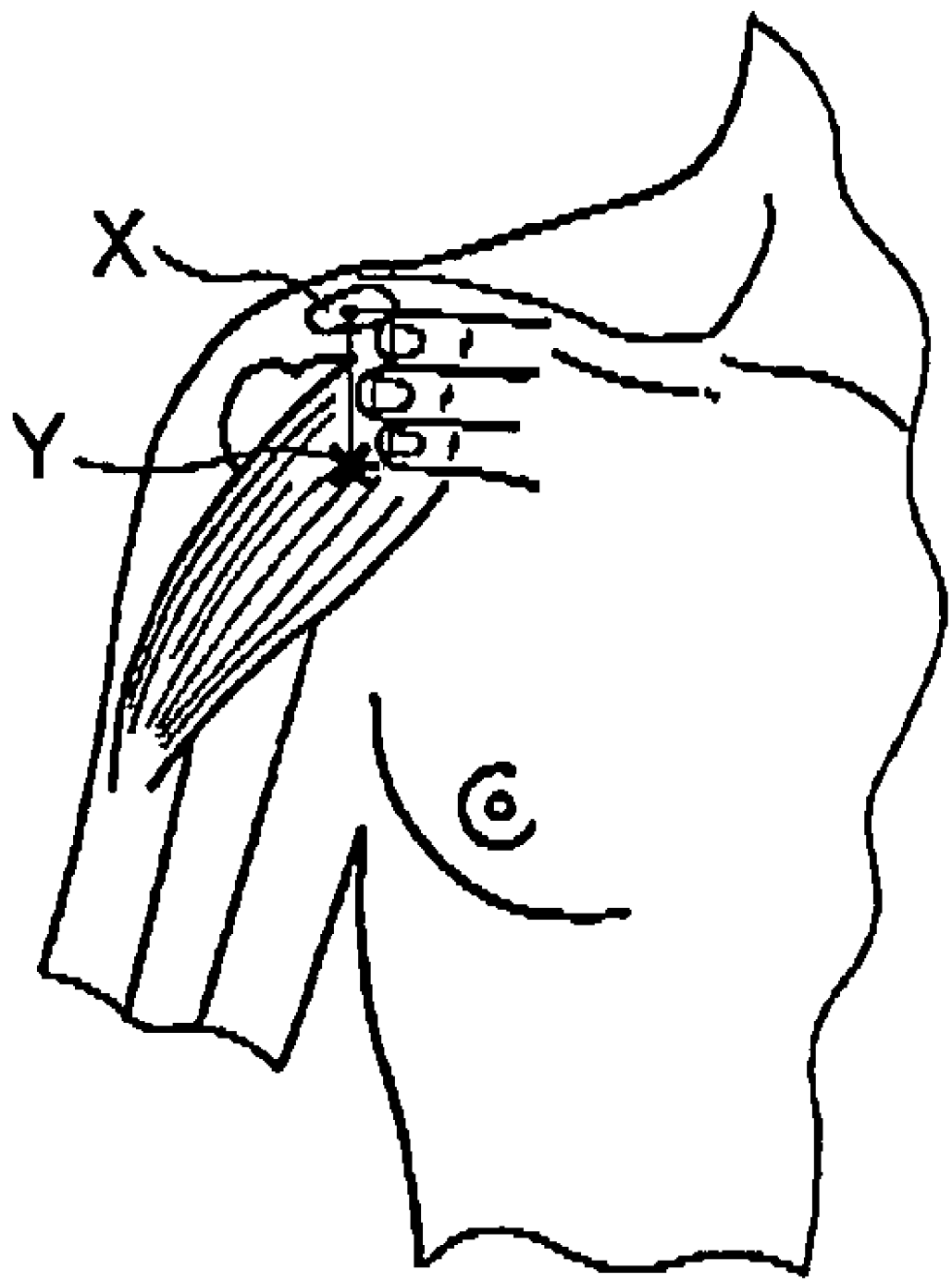
FIG. 2 is a view illustrating a method of measuring myoelectric potentials at deltoid muscles.

Although FIG. 2 shows the position at which the sensor 14 is attached to the deltoid muscle in the right shoulder, the sensor 12 is attached in the same manner to the deltoid muscle in the left shoulder.

Referring to FIGS. 3 through 7, a workability evaluation method implemented in the processing unit 20 will be described.

Figure 3:
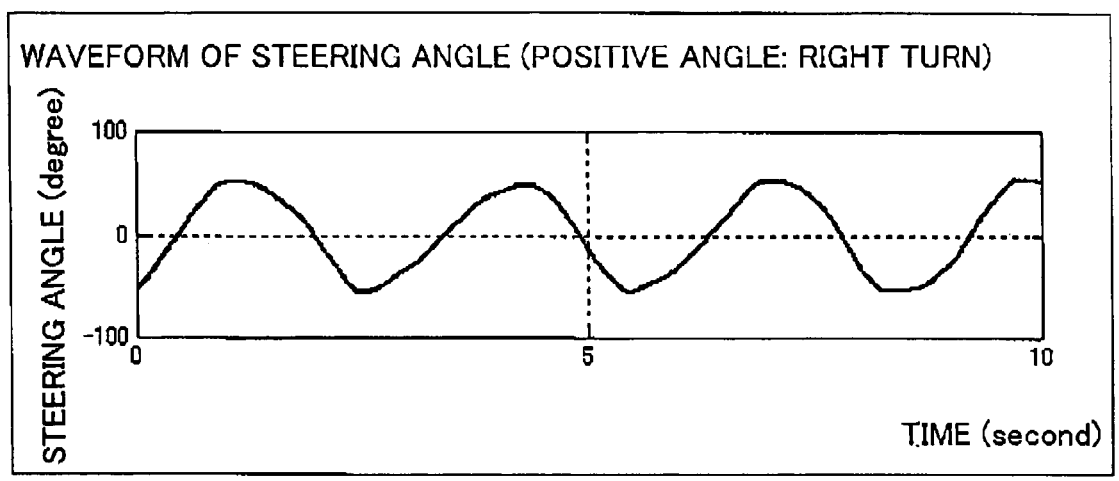
FIG. 3 is a graph showing an example of a measured waveform of a steering angle.

FIG. 3 is view showing an example of a measured waveform of a steering angle acquired by the operational displacement processor 26. The waveform is represented by assuming that the angle of a steering wheel is positive in a range extending rightward from a neutral point. The result of such measurement presents a sinusoidal curve having a substantially fixed time period, which is obtained when the steering wheel is alternately turned clockwise and counterclockwise, for example, in the case of a vehicle driving test where driving is performed along a pylon slalom course along which pylons are arranged in evenly spaced relation.

In the case where the time-series data of the operation quantity shows periodic fluctuations as described above, a sampling time for the time-series data of the first correlation coefficient, explained later, can be determined based on a basic period of the operation that has been calculated by using the period of the time-series data. In this case, a period ranging from 25% to 100% of the basic period is determined preferably as the sampling time in terms of the precision of an arithmetic operation.

In the case where periodic fluctuations do not appear in the time-series data of the operation quantity, a sampling time that has been predetermined in accordance with the operated device, operating environments, and the like can be used appropriately.

Figure 4:
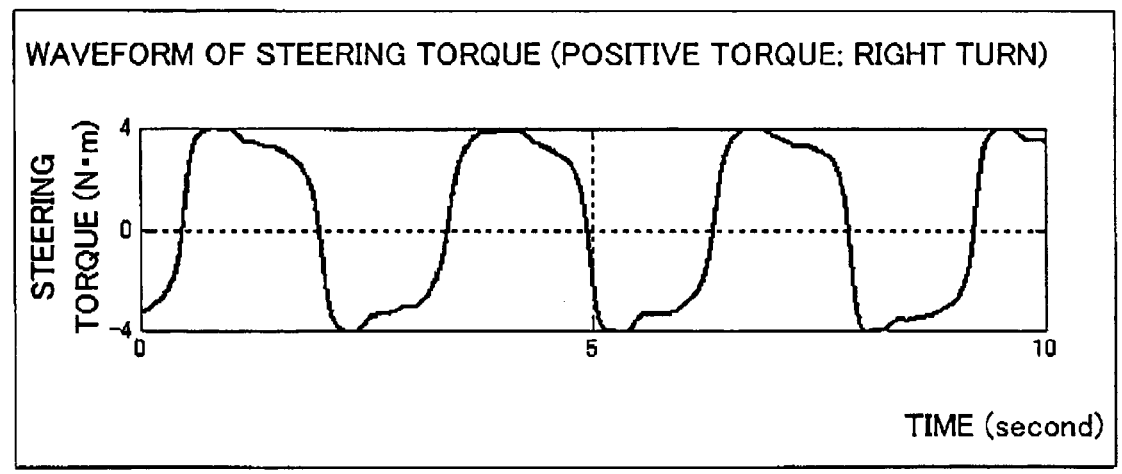
FIG. 4 is a graph showing an example of a measured waveform of a steering torque.

FIG. 4 is a view showing an example of a measured waveform of a steering torque acquired by the operational displacement processor 26. The waveform is represented by assuming that a torque placed on the steering wheel when it is turned clockwise is positive and a torque placed on the steering wheel when it is turned counterclockwise is negative.

The measured waveform of the steering torque is similar to the measured waveform of the steering angle, and has a periodicity. The basic period of the measured waveform of the steering torque is substantially equal to the basic period of the measured waveform of the steering angle, and can be used to calculate the length of the sampling time for the time-series data of the first correlation coefficient.

Figure 5A:
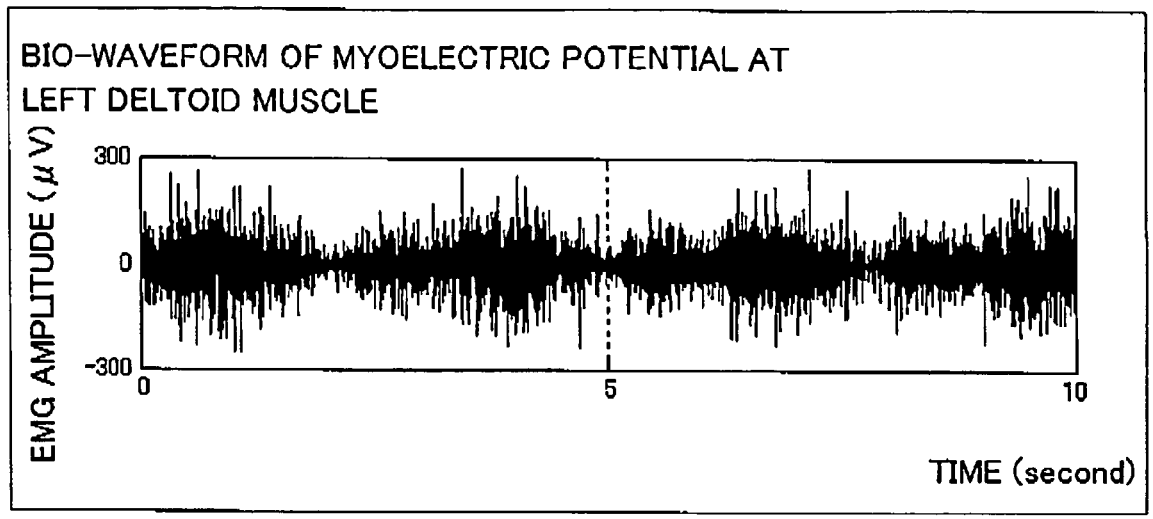
FIGS. 5A and 5B are graphs showing examples of measured waveforms of myoelectric potentials.
Figure 5B:
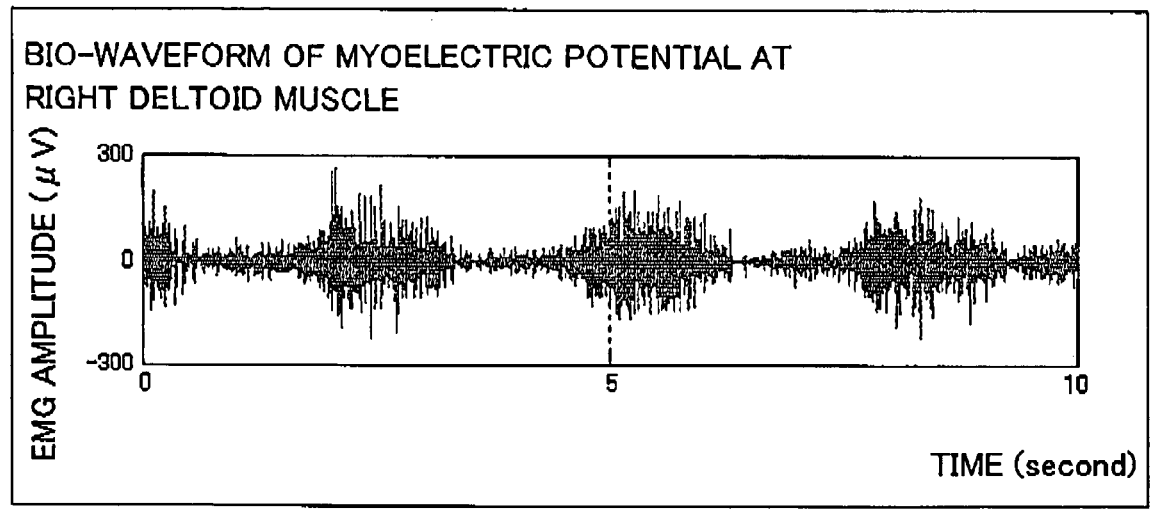

FIGS. 5A and 5B are views showing examples of measured waveforms of myoelectric potentials: FIG. 5A is a view showing the myoelectric potential at the deltoid muscle in the left shoulder of the driver, representing time-series fluctuations in the myoelectric potential; and FIG. 5B is a view showing the myoelectric potential at the deltoid muscle in the right shoulder of the driver, representing time-series fluctuations in the myoelectric potential.

After being detected by the sensor 12, the myoelectric potential at the left deltoid muscle is subjected to the removal of ambient noise and signal amplification by the bio-amplifier 18, is sent to the processing unit 20, and is displayed on the output unit 22, such as a monitor.

After being detected by the sensor 14, the myoelectric potential at the right deltoid muscle is subjected to the removal of ambient noise and signal amplification and is displayed on the output unit 22, such as a monitor.

As described above, in a pair of antagonistic muscles such as the deltoid muscles in the left and right shoulders, one of the pair of muscles contracts while the other muscle relaxes in response to the wheel steering operation by the driver.

Figure 6A:
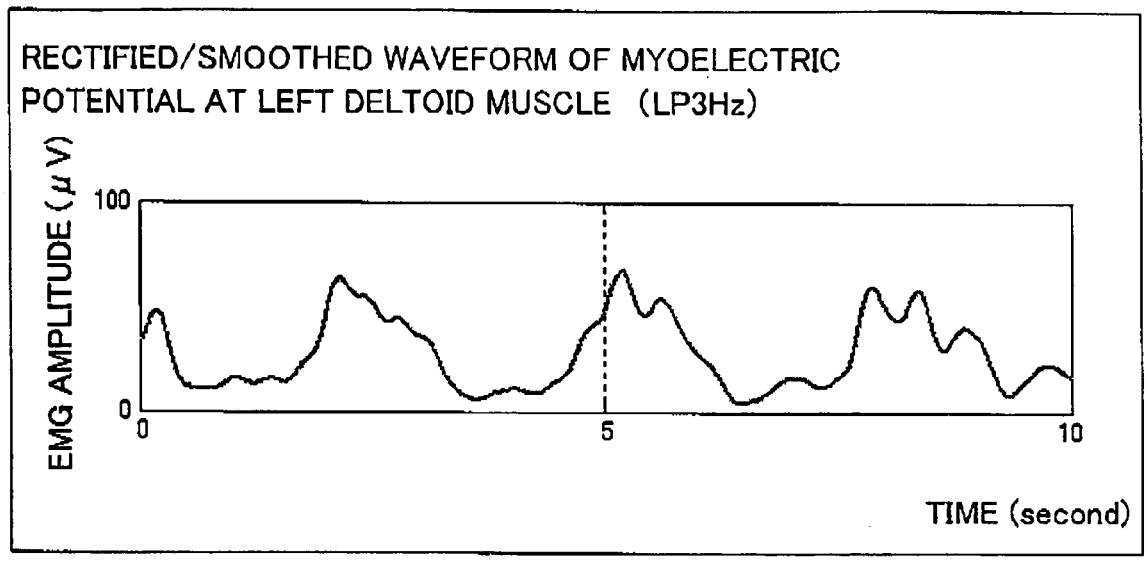
FIGS. 6A and 6B are graphs showing waveforms obtained by rectifying and smoothing the respective measured waveforms shown in FIGS. 5A and 5B.
Figure 6B:
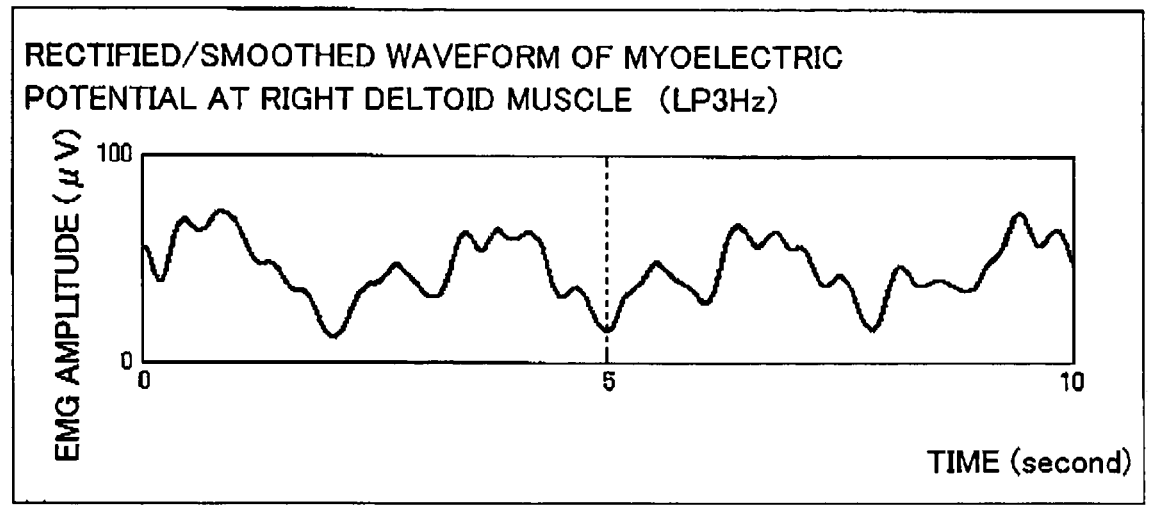

FIGS. 6A and 6B are views showing waveforms obtained by rectifying and smoothing the respective measured waveforms shown in FIGS. 5A and 5B. FIG. 6A shows a processed electromyographic waveform obtained by performing full-wave rectification on the waveform of the myoelectric potential at the deltoid muscle in the left shoulder measured in FIG. 5A, and then smoothing the resulting waveform by moving average.

FIG. 6B shows a processed electromyographic waveform obtained by rectifying the waveform of the myoelectric potential at the deltoid muscle in the right shoulder measured in FIG. 5B, and then smoothing the resulting waveform.

Although in this embodiment, the smoothing process is performed by moving average, the smoothing process may also be performed by using another technology such as low pass filtering or band pass filtering.

Figure 7:
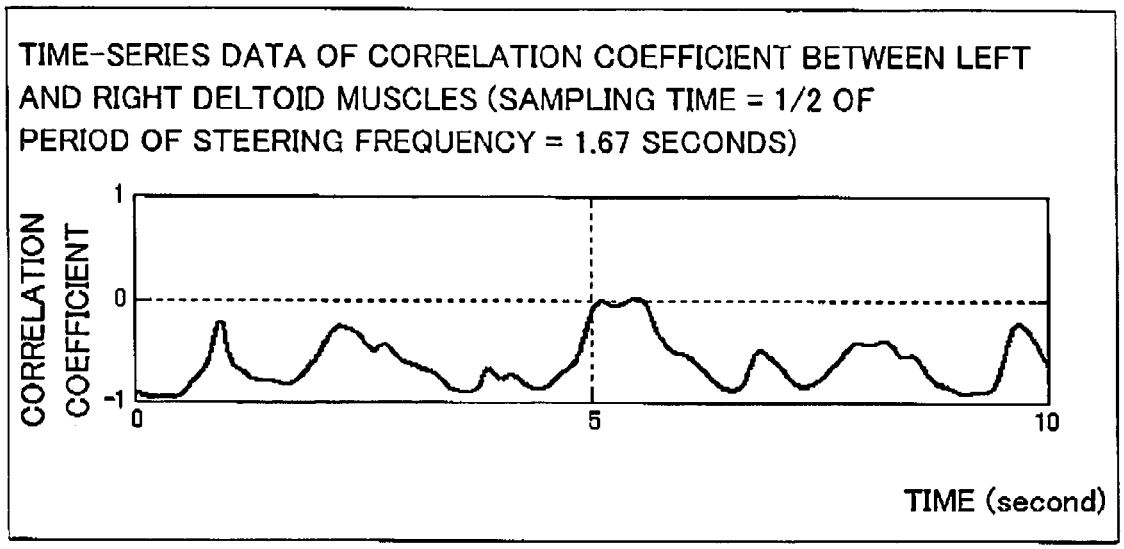
FIG. 7 is a graph showing an example of the time-series data of a correlation coefficient (the first correlation coefficient) between the waveforms shown in FIGS. 6A and 6B.

FIG. 7 is a view showing the waveform of the time-series data of the first correlation coefficient obtained from the waveforms of the myoelectric potentials of the left and right deltoid muscles shown in FIGS. 6A and 6B, which represents the time-series data of the first correlation coefficient obtained from the left and right deltoid muscles of the driver.

By using the time-series data of the calculated first correlation coefficient, the operability of the operated device is evaluated. Specifically, when the operation has been performed smoothly, the prime mover of the pair of antagonistic muscles contracts while the antagonist thereof relaxes in response to the operation, so a strong negative correlation is observed between the two myoelectric potential signals. Conversely, when the operation has not been performed smoothly due to excessive strain resulting from mental load or difficult control of the operation, the negative correlation observed between the two myoelectric potential signals is not so prominent.

Accordingly, the smoothness of the operation can be evaluated by observing the correlation between the two myoelectric potential signals by using the time-series data of the first correlation coefficient.

By evaluating the smoothness of the operation of a device in the above-described manner, it is possible to evaluate operability such as an ease of control of the operation or a magnitude of mental load resulting from the operation. When the driver is performing the wheel steering operation smoothly, it can be considered that the driver is in a comfortable condition even during the wheel steering operation, so operability in operating a device serves as a factor representing the comfortability of the operator's operation of the equipment.

In a specific method of evaluating the smoothness of an operation, for example, a histogram of values in the time-series data of the first correlation coefficient vs. the frequency distribution thereof is created, a range where the negative correlation is conceivably strong is defined, and frequencies included in the range are used, to thereby determine whether or not the smoothness of the operation is excellent.

In the case of repetitively performing an operation a plurality of times and determining which of the operations is most excellent in operability, the operation which has the highest frequency included in the range may be evaluated to be the operation which is most excellent in operability. It is also possible to predetermine a threshold for the frequencies and evaluate that those of the operations which have frequencies included in the range where the negative correlation is conceivably strong and higher than the threshold are excellent in operability.

The smoothness of the operation may also be determined from the average value of the time-series data of the first correlation coefficient. Further, it is also possible to determine whether or not the smoothness of the operation is excellent based on whether or not the minimum value of the time-series data of the first correlation coefficient has exceeded a predetermined threshold.

Although the time-series data of the first correlation coefficient has been measured in FIG. 7 assuming that the length of the sampling time is 50% of the basic period, the length of the sampling time may appropriately range from 25% to 100% of the basic period depending on the precision of the evaluation. As data on the myoelectric potential signals subjected to a specified process to be used for the calculation of the time-series data of the first correlation coefficient, all of the data from the myoelectric potential signals included in the sampling time may be used or data obtained by equidistantly selecting the processed myoelectric potential signals included in the sampling time may also be used.

Figure 8:
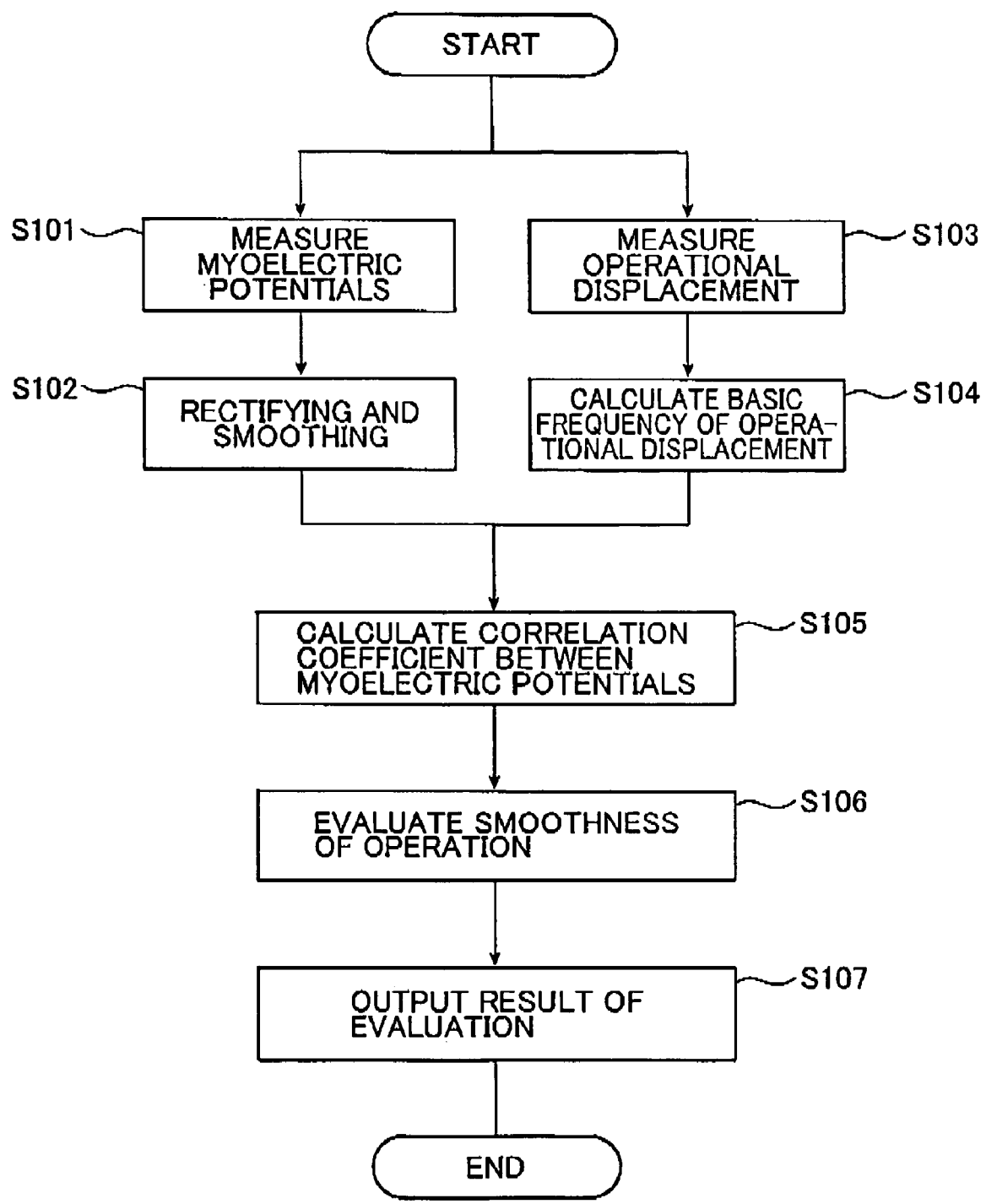
FIG. 8 is a flow chart showing a flow of a process in a workability evaluating apparatus.

FIG. 8 is a flow chart showing the flow of a process in a workability evaluating apparatus.

The myoelectric potential sensors measure the myoelectric potentials (Step S101). The sensors 12 and 14 detect myoelectric potentials at the left and right shoulders of the driver and send the myoelectric potential signals to the bio-amplifier 18. The bio-amplifier 18 removes noise from the myoelectric potential signals, amplifies the myoelectric potential signals, and sends the myoelectric potential signals to the processing unit 20.

The processing unit rectifies and smoothes the myoelectric potential signals (Step S102). In the processing unit 20, the myoelectric potential processor 24 receives the myoelectric potential signals, rectifies and smoothes the myoelectric potential signals, and sends them to the arithmetic operation unit 25.

The operation quantity detector measures an operational displacement (Step S103). The operation quantity detector 19 detects the steering angle as a quantity of the operational displacement and sends the operational displacement signal to the processing unit 20.

The processing unit calculates the primary frequency of the operational displacement (Step S104). In the processing unit 20, the operational displacement processor 26 receives the operational displacement signal and calculates the primary frequency, i.e., basic frequency of the operational displacement signal. In the calculation, frequency analysis is performed by using, e.g., the FFT (Fast Fourier Transformation) or the like.

Upon judging that the operational displacement signal is periodically fluctuating, the operational displacement processor 26 determines the sampling time by using the basic frequency and sends information on the sampling time to the arithmetic operation unit 25. Preferably, the sampling time ranges from 25% to 100% of the period of the basic frequency, such as 100%, 50%, or 25% of the period of the basic frequency.

When there is no periodicity in the operational displacement signal, the information on the sampling time is information indicating that there is no periodicity in the quantity of the operational displacement so that sampling is performed in a time predetermined depending on the operated device, operating environments, and the like.

The arithmetic operation unit calculates the first correlation coefficient between the myoelectric potentials (Step S105). The arithmetic operation unit 25 receives the information on the sampling time sent from the operational displacement processor 26 and calculates the first correlation coefficient between the smoothed myoelectric potential signals in the sampling time.

The arithmetic operation unit evaluates the smoothness of the operation (Step S106). The arithmetic operation unit 25 evaluates the smoothness of the operation by using the calculated first correlation coefficient and sends the result of the evaluation to the output unit 22.

The smoothness evaluation of the operation can be executed based on the frequency of the presence of each of values in the time-series data of the first correlation coefficient in a specified range, on the average value of the time-series data of the first correlation coefficient, or on the minimum value of the time-series data of the first correlation coefficient.

The output unit outputs the result of the evaluation (Step S107). As the output unit 22, there can be a display unit such as a display or monitor, a memory unit, or a control unit.

When the output unit 22 is a display unit, the result of the evaluation is displayed on a display, a monitor, or the like and presented to a user so that the user is allowed to perform in-situ evaluation of the smoothness of the operation of the operated equipment.

When the output unit 22 is a memory unit, the result of the evaluation is provisionally stored in the memory unit. The user is allowed to take the memory unit with him or her to a laboratory or the like after the end of the operation of the equipment and examine the result of the evaluation.

When the output unit 22 is a control unit, a signal responsive to the result of the evaluation is transmitted to the control unit so that various devices are controlled based on the signal. When the result of the evaluation is outputted to an electronic control unit (ECU) mounted on a vehicle, e.g., the ECU is allowed to perform a control operation for avoiding danger such as the correction of control/intervention conditions for the vehicle or the correction of a control gain in accordance with the result of the evaluation.

The embodiment described above has evaluated the operability of a device by attaching the myoelectric potential sensors 12 and 14 to the deltoid muscles in the left and right shoulder portions and calculating the time-series data of the first correlation coefficient obtained from the left and right deltoid muscles. However, the present invention can also evaluate the operability of a device by calculating the time-series data of the first correlation coefficients associated with myoelectric potential signals from two or more pairs of antagonistic muscles.

Figure 9:
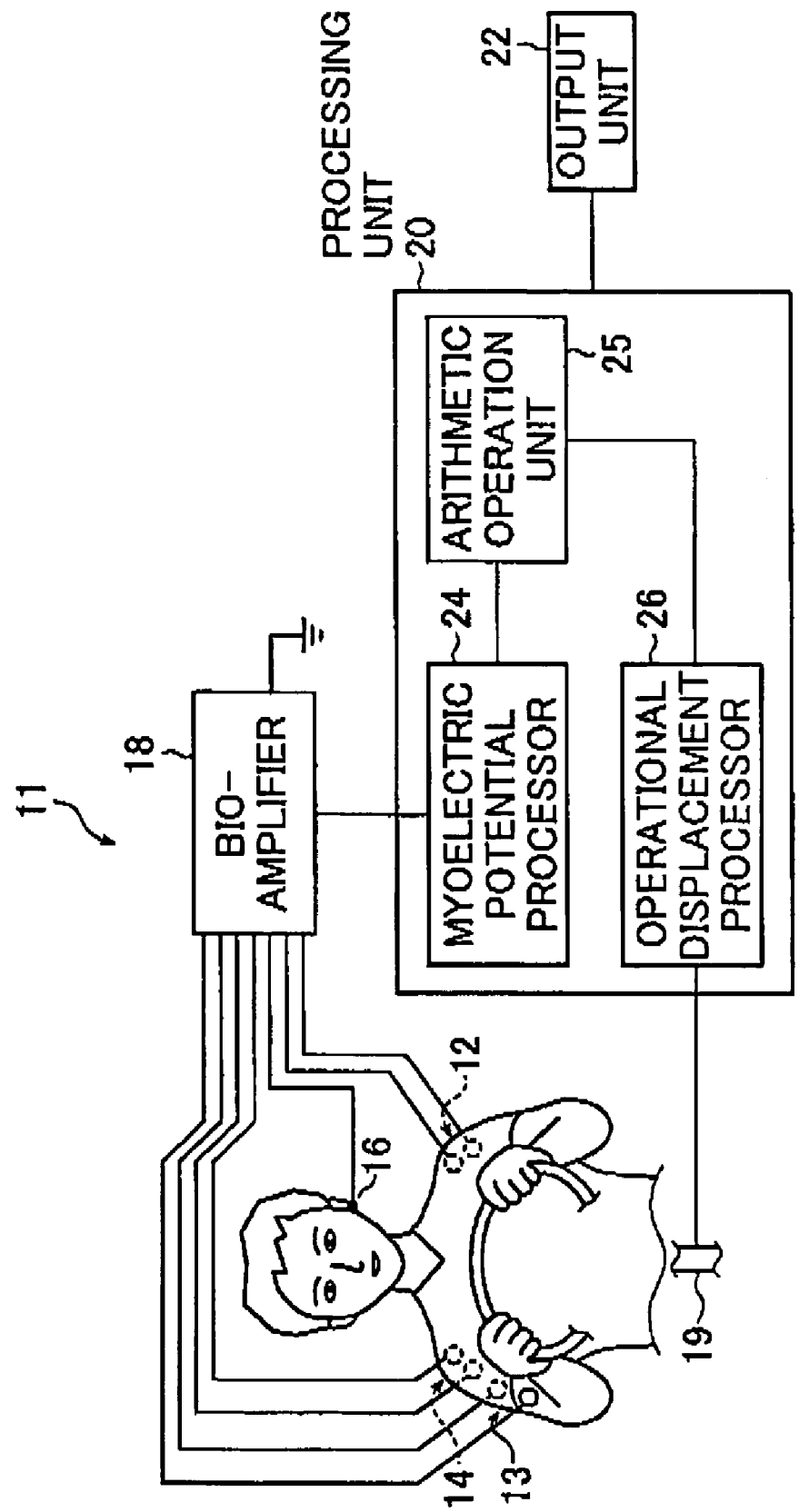
FIG. 9 is a structural view showing another example of when the workability evaluating apparatus is used to evaluate operability during a driving of a vehicle.

Referring to FIG. 9, a method of evaluating the operability of a device by measuring myoelectric potentials at two pairs of antagonistic muscles will now be described.

The myoelectric potentials at the two pairs of antagonistic muscles are detected by using myoelectric potential sensors 12, 13, and 14 so that two time-series data of the first correlation coefficients are calculated. By calculating a correlation coefficient (the second correlation coefficient) between the two calculated time-series data of the first correlation coefficients, the operability of the device is evaluated. As for the components of the workability evaluating apparatus shown in FIG. 9 that correspond to those of the workability evaluating apparatus shown in FIG. 1, the description thereof will be omitted, and the same reference numerals will be used.

The workability evaluating apparatus 11 includes: sensors 12 and 14 for detecting myoelectric potentials at the left and right deltoid muscles of a driver as a subject under measurement; sensors 13 and 14 for measuring myoelectric potentials at the right deltoid muscle of the driver and the right triceps muscle of the driver; a ground electrode 16; a bio-amplifier 18 for amplifying each of the myoelectric potentials obtained from the sensors 12, 13, and 14; an operation quantity detector 19 for detecting the displacement of the operated device; a processing unit 20 for evaluating workability based on the time-series waveforms of the myoelectric potentials detected at the deltoid and triceps muscles; and an output unit 22 for displaying the result of the evaluation.

Since the ground electrode 16, the bio-amplifier 18, and the operation quantity detector 19 are the same as in the workability evaluating apparatus shown in FIG. 1, the description thereof will be omitted.

The myoelectric potential sensors are attached not only to the left and right deltoid muscles of the driver but also to the right triceps muscle of the driver. The right triceps muscle of the driver is a muscle located on the rear surface of the brachial portion of the driver's right arm, and is used to stretch and extend the elbow joint.

In the operation of equipment such as the steering wheel of a vehicle during the driving of a vehicle, therefore, the right triceps muscle and the right deltoid muscle antagonize each other in the same manner as the left and right deltoid muscles.

The structure of the sensor 13 and the attachment thereof to the surface of the skin are the same as those of the electromyographic sensors 12 and 14.

In terms of hardware, the processing unit 20 includes: a CPU; a RAM; a ROM; and a HDD, similarly to the processing unit 20 shown in FIG. 1. In terms of software, the processing unit 20 has a myoelectric potential processor 24; an operational displacement processor 26; and an arithmetic operation unit 25. However, the arithmetic operation unit 25 performs a process, which will be described later.

Referring to FIGS. 10 to 14, a method for evaluating workability which is implemented in the processing unit 20 will be described.

Figure 10:
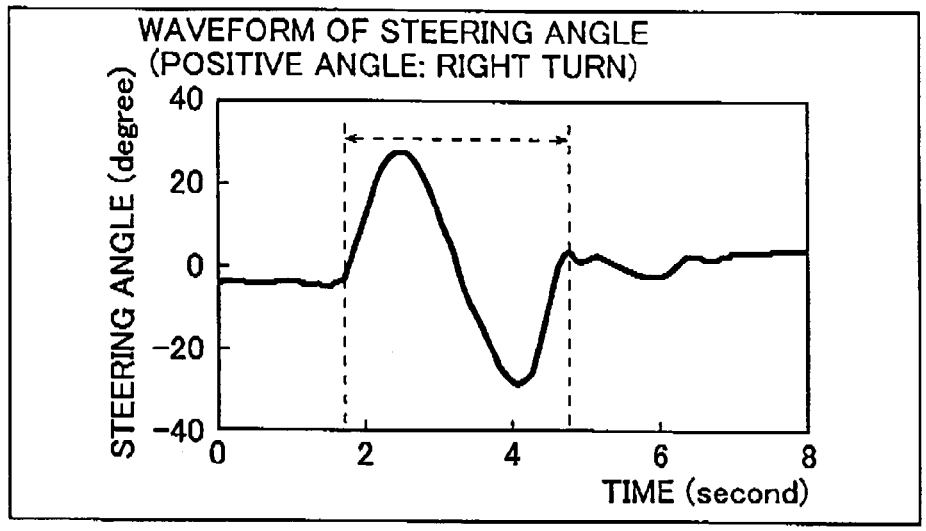
FIG. 10 is a graph showing another example of a measured waveform of a steering angle.

FIG. 10 is a view showing an example of a measured waveform of a steering angle acquired by the operational displacement processor 26. The measured waveform of the steering angle is the time-series data of an operation quantity, which is represented by assuming that the angle of a steering wheel is positive in the rightward direction. Such a result of measurement presents a sinusoidal curve having a substantially fixed time period, which is obtained when, e.g., a vehicle drives along a course in which pylons are aligned in a row in evenly spaced relation by weaving through the pylons (during slalom driving).

Figure 11:
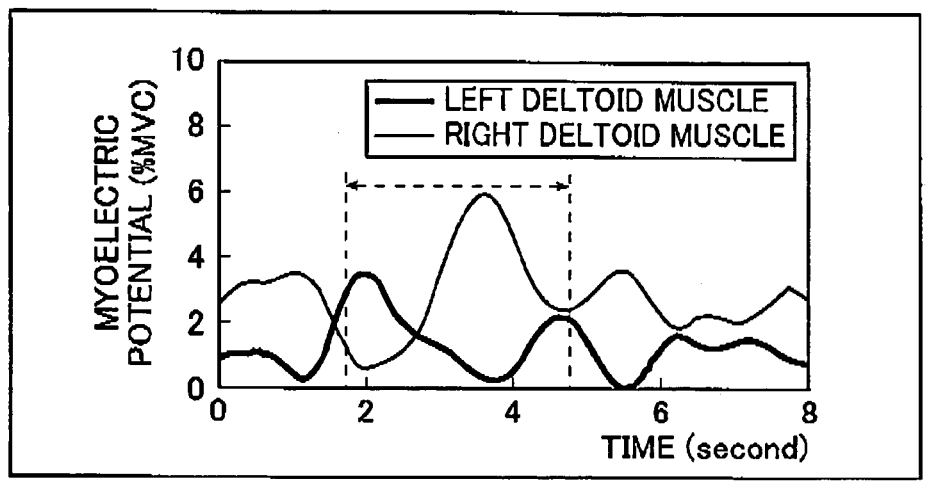
FIG. 11 is a graph showing an example of measured waveforms of myoelectric potentials.

The broken lines in FIG. 11 indicate one time period in the measured waveform of the steering angle, which is the basic period of the operation. The basic period serves as a sampling time for the time-series data of the first correlation coefficient, which will be described later.

Figure 12:
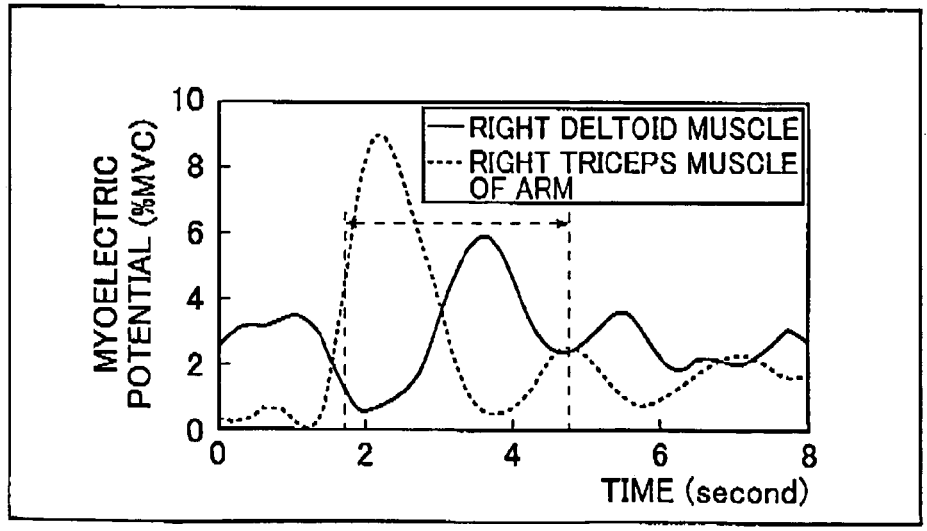
FIG. 12 is a graph showing an example of measured waveforms of the myoelectric potentials.

FIG. 11 shows processed electromyographic waveforms obtained by performing full-wave rectification on waveforms of myoelectric potentials at the left and right deltoid muscles, and then smoothing the waveforms by moving average. FIG. 12 shows processed electromyographic waveforms obtained by performing full-wave rectification on waveforms of myoelectric potentials at the right deltoid muscle and the right triceps muscle, and then smoothing the waveforms by moving average. In the drawings, the broken lines indicate the basic period of the operation calculated from the measured waveform of the steering angle.

Such processed waveforms are obtained by performing processes, such as the removal of ambient noise and the amplification of signals of the myoelectric potential signals detected by the myoelectric potential sensors and displaying the processed waveforms on the output unit such as a monitor. Each of the myoelectric potentials is represented by the ratio of a muscle activity to a maximum voluntary contraction (% MVC).

Figure 13A:
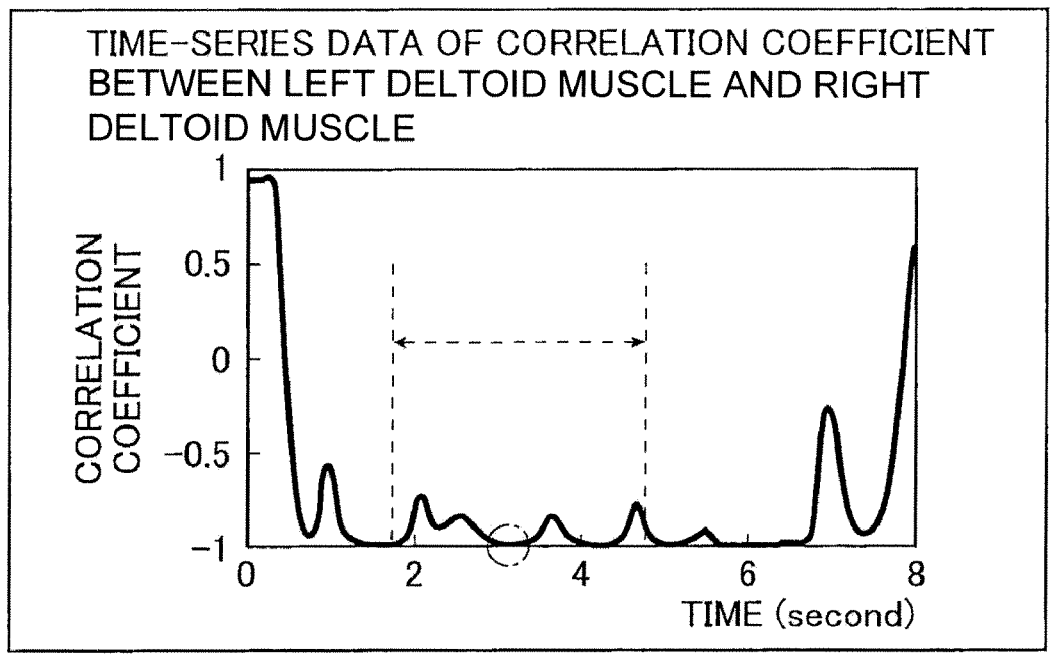
FIGS. 13A and 13B are graphs showing other examples of the time-series data of the first correlation coefficient.
Figure 13B:
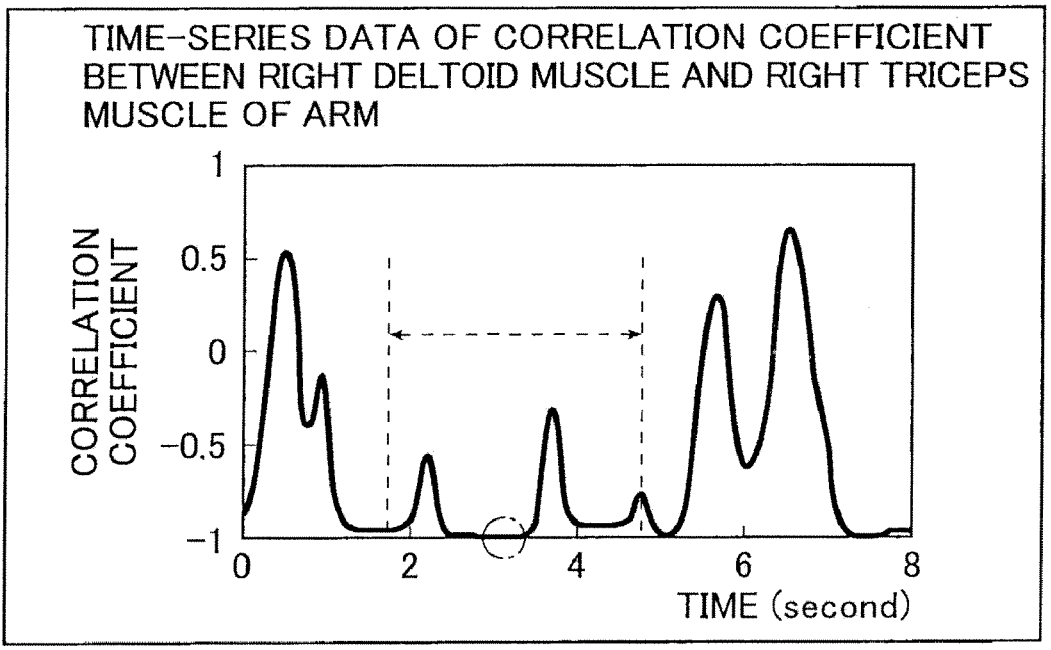
Figure 14A:
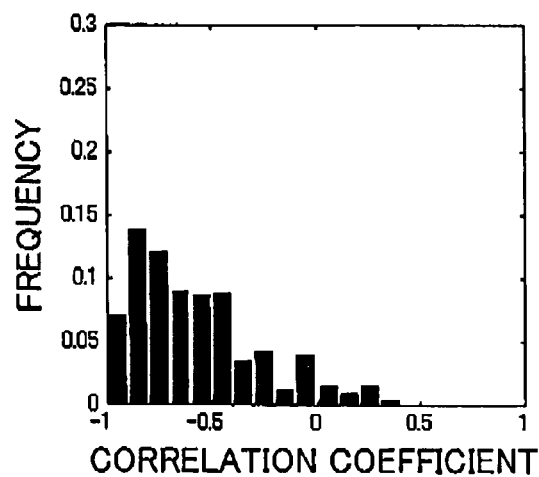
FIGS. 14A to 14E are graphs showing histograms of time-series data of the first correlation coefficient between myoelectric potential signals detected from a subject 1 under measurement.
Figure 14D:
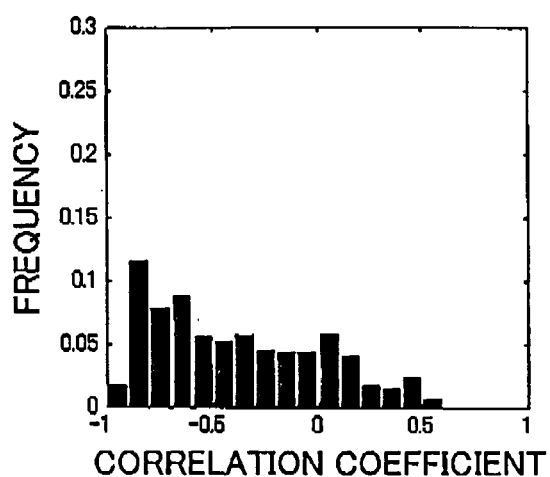
Figure 14B:
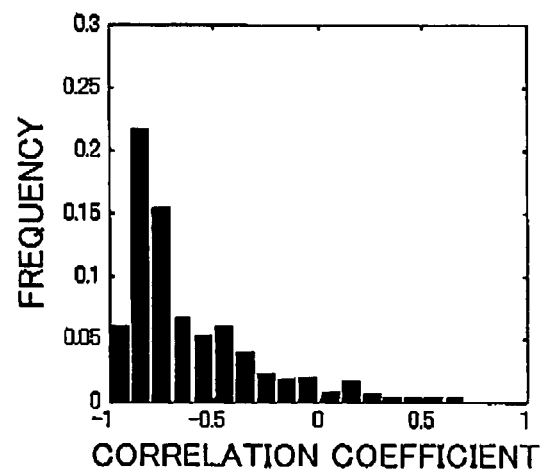
Figure 14E:
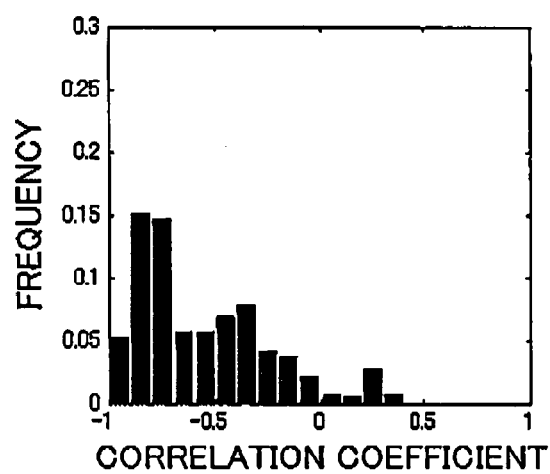
Figure 14C:
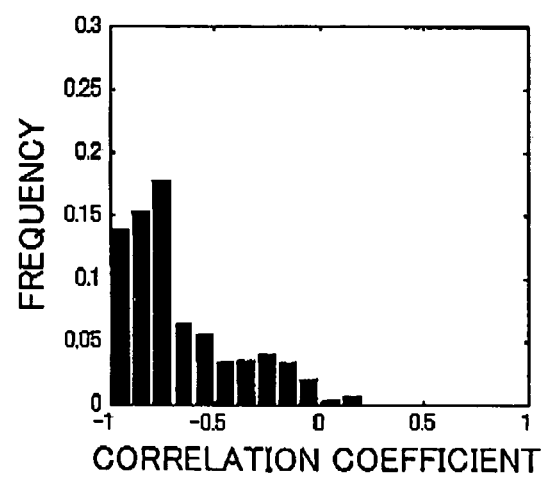
Figure 15A:
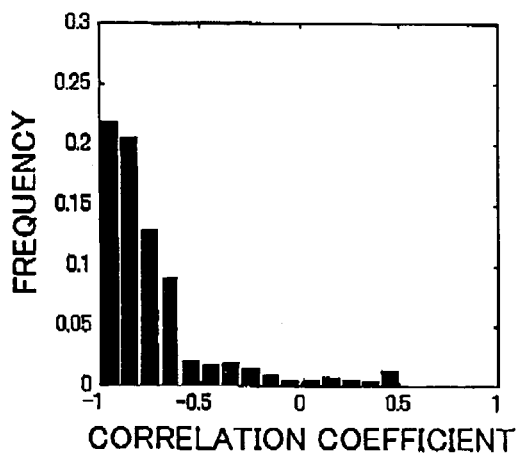
FIGS. 15A to 15E are graphs showing histograms of time-series data of the first correlation coefficient between myoelectric potential signals detected from a subject 2 under measurement.
Figure 15D:
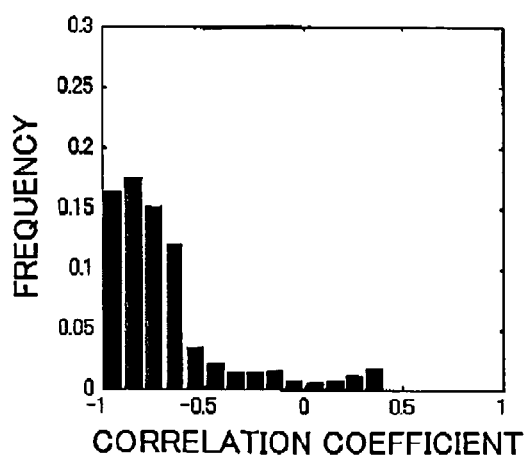
Figure 15B:
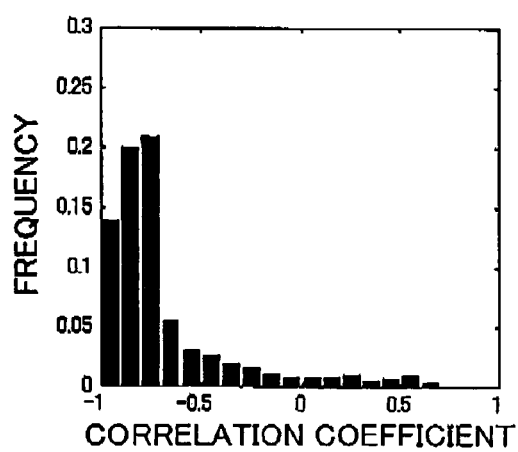
Figure 15E:
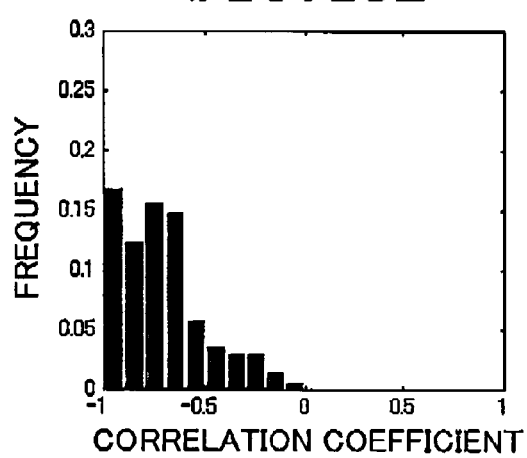
Figure 15C:
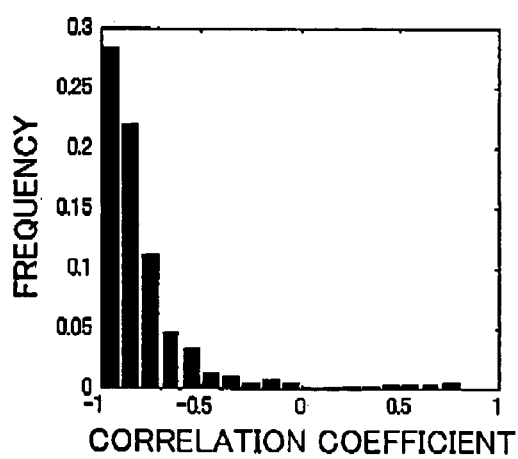

FIGS. 13A and 13B are views showing the waveforms of the time-series data of the first correlation coefficients obtained from the respective pairs of muscles shown in FIGS. 11 and 12. FIG. 13A shows the time-series data of the first correlation coefficient calculated based on the processed waveforms of the myoelectric potentials at the left and right deltoid muscles and FIG. 13B shows the time-series data of the first correlation coefficient calculated based on the processed waveforms of the myoelectric potentials at the right deltoid muscle and the right triceps muscle.

In the drawings, the broken lines indicate the basic period of the operation calculated from the measured waveform of the steering angle shown in FIG. 10.

The embodiment described above has examined the first correlation between two myoelectric potential signals by using the time-series data of the correlation coefficient obtained from a pair of antagonistic muscles to evaluate the smoothness of an operation. By contrast, this embodiment evaluates the smoothness of an operation by examining the correlations between myoelectric potential signals from two pairs of antagonistic muscles.

In a steering operation in a vehicle or the like shown in FIG. 9, the two pairs of antagonistic muscles are the pair of right and left deltoid muscles and the pair of the right deltoid muscle and the right triceps muscle.

Thus, in the operator's operation of equipment involving antagonism between the left and right parts of a body, the operation of the equipment is performed through the interaction between left and right antagonistic muscles and between antagonistic muscles in the right (or left) part of the body. Accordingly, the examination of the correlation between the two pairs of antagonistic muscles, which are the pair of left and right antagonistic muscles and the pair of antagonistic muscles in the right (or left) part of the body, allows for the evaluation of the smoothness of an operation.

In the time-series data of the first correlation coefficient from a pair of antagonistic muscles, operability is more excellent as the negative correlation (the first correlation coefficient approaches −1) is stronger and fluctuations are smaller. In that case, the smoothness of the operation is excellent.

By contrast, as the positive correlation (the second correlation coefficient approaches +1) between the two time-series data of the first correlation coefficients from the two pairs of muscles is stronger, disturbances in the coordination between one of the two pairs of muscles are more synchronous with those in the coordination between the other pair of muscles. The synchronization of the coordination disturbances indicates that the operation involves a strain so that the smoothness of the operation is not excellent.

In the evaluation of the smoothness of the operation, therefore, the two time-series data of the first correlation coefficients associated with myoelectric potential signals from the two pairs of antagonistic muscles are produced and the second correlation coefficient between the two time-series data is calculated. When a strong positive correlation is observed, it is judged that the operator's operation of the equipment is not smooth. When a strong negative correlation is observed, it can be judged that the operator's operation of the equipment is smooth.

By thus evaluating the smoothness of the operator's operation of the equipment by using the plural time-series data of the first correlation coefficients associated with myoelectric potential signals from two or more pairs of antagonistic muscles, it becomes possible to more precisely evaluate operability such as the ease of control of the operation or the magnitude of a mental load resulting from the operation.

The operability of the operation of the equipment also serves as a factor representing the comfortability of the operation of the equipment.

EXAMPLE 1

Subjects under measurement drove vehicles equipped with tires having different specifications, and myoelectric potentials were measured so that the smoothness of operating the vehicles could be evaluated. Then, the subjects under measurement performed actual subjective evaluations so that the reliability of the smoothness evaluation of the operations based on the myoelectric potentials was examined.

The course used for evaluation is a linear portion of a circulating road in a test course. The driving task was such that two subjects under measurement drove along a pylon slalom at a speed of 100 km/h. The spacing between pylons was 45 m and an asphalt-paved road with a dry surface was used. The vehicles used for the test were 4-door sedans.

The tires mounted on the test vehicles are of three types (tires a, b, and c), the respective sizes, air pressures, and cornering powers of which are shown below in Table 1.

TABLE 1

| | Tires Under Test | | |
|---|---|---|---|
| | Tire a | Tire b | Tire c |
| Size | 215/55R16 | 195/65R15 | 225/45R17 |
| Air Pressure (kPa) | 210 | 190 | 220 |
| Cornering power (kN/deg) | 1.37 | 1.26 | 1.70 |

Five vehicles equipped with different types of tires were prepared, including a reference vehicle. Since the smoothness of an operation associated with the steering wheel of a vehicle is influenced by the tires mounted thereon, the prepared vehicles are different in operability.

The specifications of the vehicles are determined by the combinations of the three types of tires. The combinations are shown below in Table 2.

TABLE 2

| | Vehicle Specs | | | | |
|---|---|---|---|---|---|
| | Reference | Spec A | Spec B | Spec C | Spec D |
| Front Tire | a | b | c | c | b |
| Rear Tire | a | b | c | b | c |

FIGS. 14A to 14E are graphs showing histograms of the time-series data of the first correlation coefficient between myoelectric potential signals detected from a subject 1 under measurement, which represent the relationships between the time-series data of the first correlation coefficient and the frequency distribution thereof. The frequency distribution of the time-series data of the first correlation coefficient indicates the number of times each of values in the time-series data of the first correlation coefficient is detected within a specified evaluation time. For example, if the negative correlation is strong throughout measurement, the frequency of the values (e.g., −1 to −0.9) in the time-series data of the first correlation coefficient indicating the correlation is high. If the negative correlation is observed only locally, the frequency is low.

FIGS. 14A to 14E are graphs based on myoelectric potentials detected from the subject 1 under measurement when he or she drove the vehicles equipped with the reference tire and the tires in the specs A to D. FIGS. 15A to 15E are graphs showing histograms of the time-series data of the first correlation coefficient between myoelectric potential signals detected from a subject 2 under measurement. FIGS. 15A to 15E are based on the myoelectric potentials detected from the subject 2 under measurement when he or she drove the vehicles equipped with the reference tire and the tires in the specs A to D.

Of the histograms of the time-series data of the first correlation coefficients mentioned above, the ones in which the time-series data of the first correlation coefficient ranges from −1 to −0.9 were considered to have a strong negative correlation, and the frequency in this range was calculated. The result of evaluation based on this frequency is shown in Table 3. The frequency is represented on the assumption that the frequency of the reference tire is 1.

TABLE 3

| | | Spec No. | | | | |
|---|---|---|---|---|---|---|
| | | Reference | Spec A | Spec B | Spec C | Spec D |
| | Front Tire | a | b | c | c | b |
| | Rear Tire | a | b | c | b | c |
| Subject 1 | Frequency | 1 | 0.86 | 1.95 | 0.26 | 0.75 |
| Subject 2 | Frequency | 1 | 0.63 | 1.31 | 0.75 | 0.77 |

From Table 3, it will be understood that the frequency associated with the tires in the spec B is the highest with each of the subjects 1 and 2 under measurement. In accordance with evaluation based on the frequencies with which the first correlation coefficients associated with the myoelectric potentials are in a specified range, the operability was most excellent when the vehicle equipped with the tires in the spec B was operated. Conversely, the operabilities of the vehicles equipped with the tires in the specs A, C, and D were less preferable than the operability of the vehicle equipped with the reference tires.

Next, the subjects under measurement performed actual subjective evaluations so that the reliability of the smoothness evaluation of the operations based on myoelectric potentials using the time-series data of the first correlation coefficient was examined.

The subjective evaluation pertains to grip feeling which is felt by the subjects under measurement, the results of which are shown in Table 4. The subjective evaluations were performed on a 1-to-10 scale. The evaluation rating is higher as the grip feeling is superior, while the evaluation rating is lower as the grip feeling is inferior.

TABLE 4

| | | Spec No. | | | | |
|---|---|---|---|---|---|---|
| | | Reference | Spec A | Spec B | Spec C | Spec D |
| | Front Tire | a | b | c | c | b |
| | Rear Tire | a | b | c | b | c |
| Subject 1 | Grip Feeling | 5 | 3 | 6 | 2 | 4 |
| Subject 2 | Grip Feeling | 6 | 4 | 7 | 4 | 2 |

From Table 4, it will be understood that the evaluation rating of the tires in the spec B was the highest with each of the subjects 1 and 2 and that the operability was the most excellent when the vehicle equipped with the tires in the spec B was operated. Conversely, the operabilities of the vehicles equipped with the tires A, C, and D were lower in evaluation rating than the operability of the vehicle equipped with the reference tires.

Thus, the result of the subjective evaluations performed by the subjects under measurement are the same as the result of evaluation based on the frequencies with which the first correlation coefficients associated with the myoelectric potentials are in a specified range. Accordingly, it can be considered that the reliability of the smoothness evaluations based on the myoelectric potential signals using the time-series data of the first correlation coefficient is high.

Figure 16A:
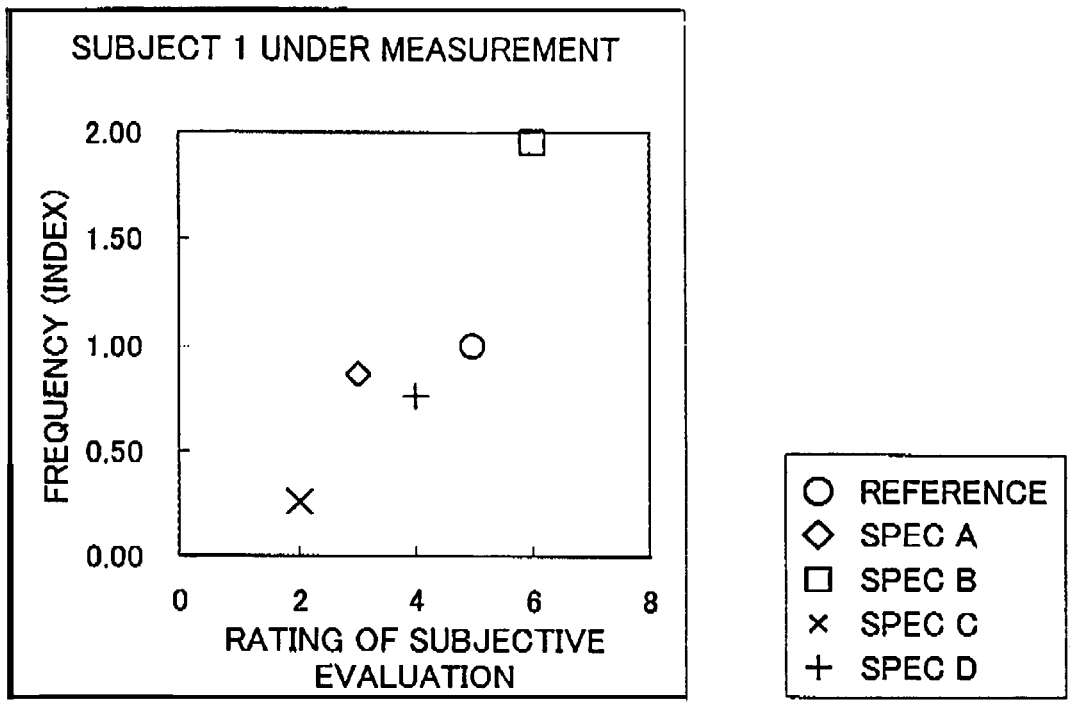
FIGS. 16A and 16B are graphs showing correspondences between subjective evaluations by the subjects under measurement and frequencies according to the time-series data of the first correlation coefficients.
Figure 16B:
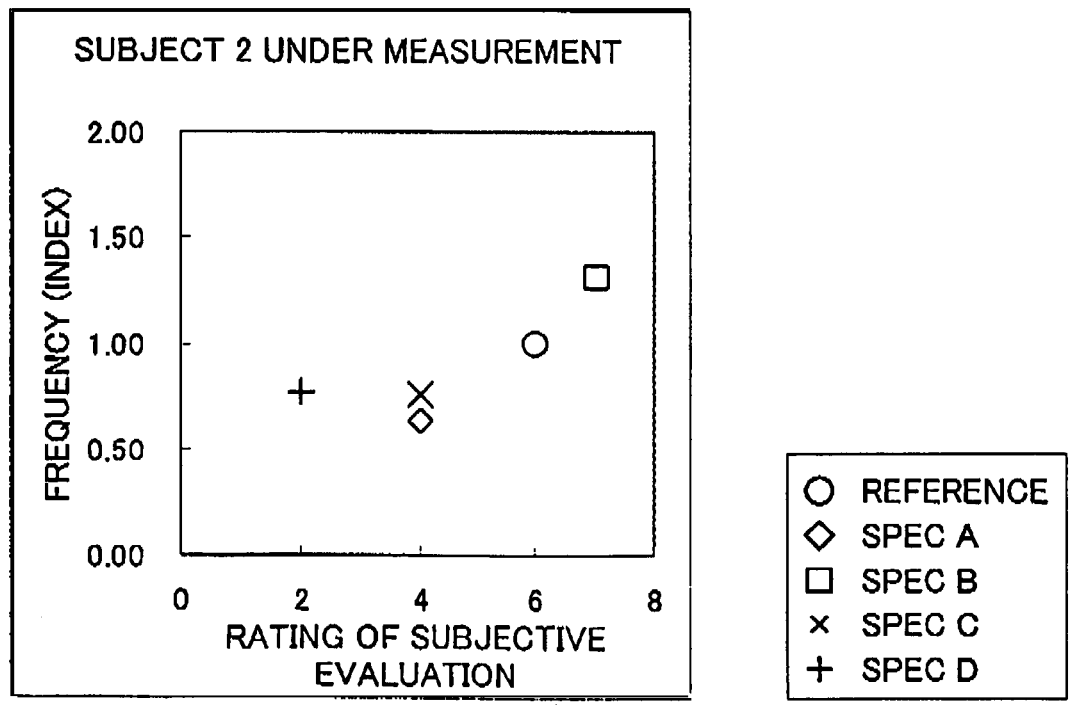

Graphs showing the correspondence between the subjective evaluations by the subjects under measurement and frequencies according to the time-series data of the first correlation coefficient are shown in FIGS. 16A and 16B. FIG. 16A shows the relationship between the rating of the subjective evaluation performed by the subject 1 under measurement and the frequency according to the time-series data of the first correlation coefficient and FIG. 16B shows the relationship between the rating of the subjective evaluation by the subject 2 under measurement and the frequency according to the time-series data of the first correlation coefficient.

From FIG. 16A, it will be understood that, as the rating of the subjective evaluation is lower, the frequency is lower and, as the rating of the subjective evaluation is higher, the frequency is higher. Accordingly, the rating of the subjective evaluation and the frequency are substantially proportionally related. In FIG. 16B, the rating of the subjective evaluation and the frequency are substantially proportionally related, except for the spec D.

From the foregoing, it will be understood that smoothness evaluations based on myoelectric potential signals using time-series data of the first correlation coefficients are substantially the same as subjective evaluations based on the perceptions of subjects under measurement. Hence, the smoothness of an operation can be evaluated quantitatively by using myoelectric potentials.

Although the operability of equipment has been evaluated based on the time-series data of the first correlation coefficient associated with the myoelectric potential signals from a pair of antagonistic muscles, the operability of equipment can also be evaluated based on myoelectric potential signals from two or more pairs of antagonistic muscles.

Exemplary combinations of the pairs of antagonistic muscles can include one pair of left and right deltoid muscles (anterior/middle/posterior), left and right biceps muscles, left and right triceps muscles (caput longum/caput laterale/caput mediale), left and right greater pectoral muscles, left and right broadest muscles of the back, either one of the left and right deltoid muscles (anterior/middle/posterior) or either one of the left and right triceps muscles (caput longum/caput laterale/caput mediale), one pair of biceps muscles, greater pectoral muscles, and broadest muscles of the back. Alternatively, the combination of the pairs of antagonistic muscles may also be an arbitrary combination of the pairs of muscles listed above.

EXAMPLE 2

A subject under measurement drove vehicles equipped with tires having different specifications, and myoelectric potentials were measured so that the smoothness of operation was evaluated. Then, the subject under measurement performed actual subjective evaluations so that the reliability of the smoothness evaluation of the operations based on the myoelectric potentials was examined.

The course used for evaluation had a length of 40 m. While driving on a lane, the subject under measurement performed a single lane change from the left lane to the right lane over a changing lane width of 4 m. The test tires mounted on the vehicles are of three types (tires A, B, and C).

Myoelectric potentials and steering angles were detected from the subject under measurement while he or she drove the vehicles equipped with the tires A, B, and C.

Figure 17A:
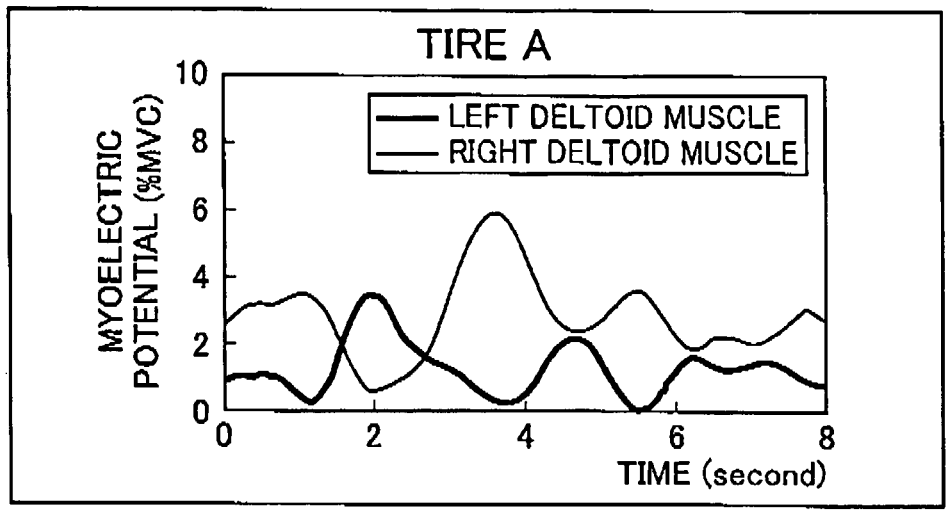
FIGS. 17A to 17C are graphs showing respective measured waveforms of a steering angle and myoelectric potentials when a vehicle equipped with tires A was driven.
Figure 17B:
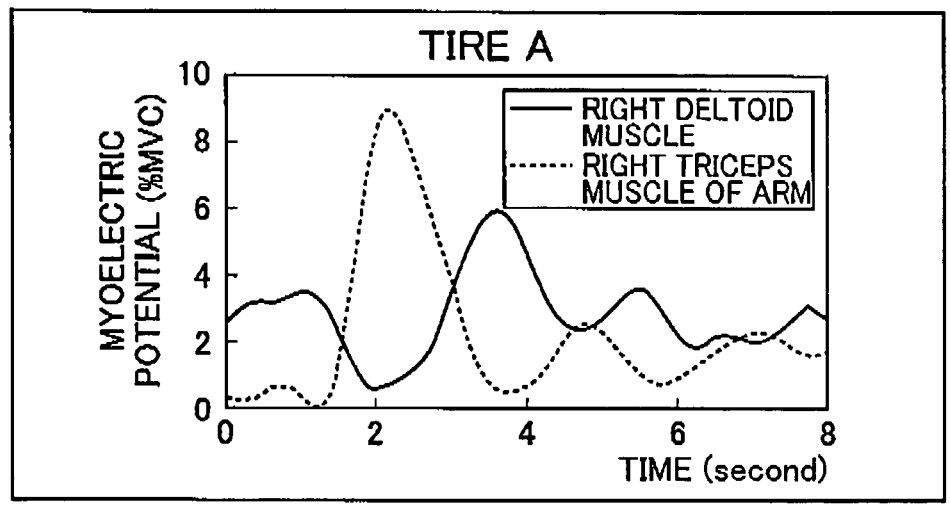
Figure 17C:
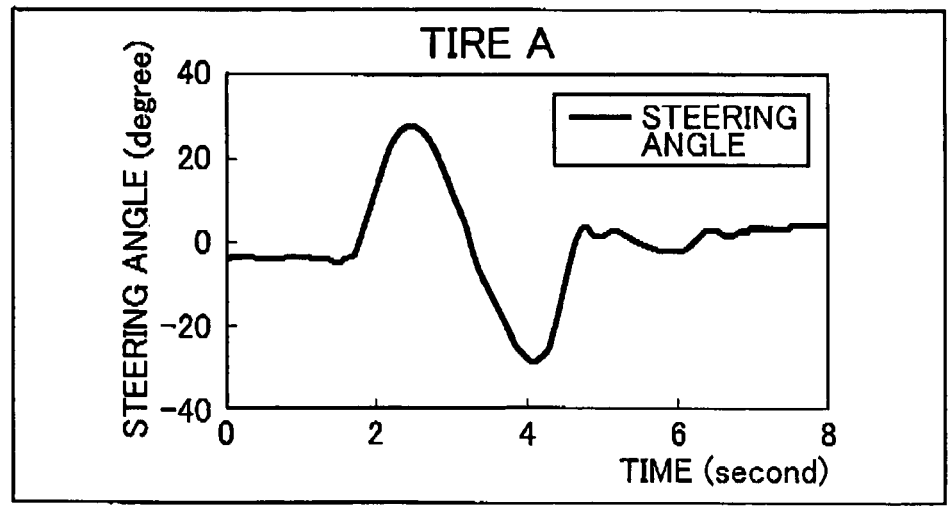
Figure 18A:
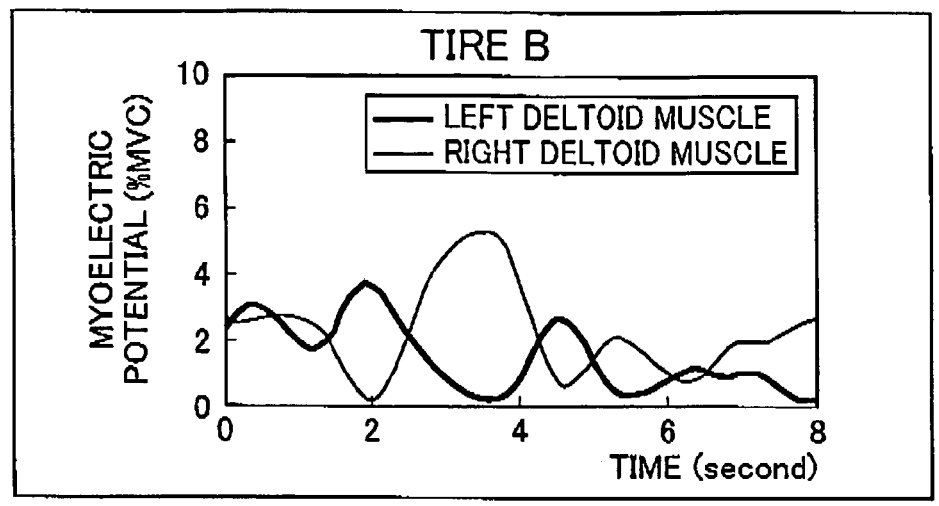
FIGS. 18A to 18C are graphs showing respective measured waveforms of a steering angle and myoelectric potentials when a vehicle equipped with tires B was driven.
Figure 18B:
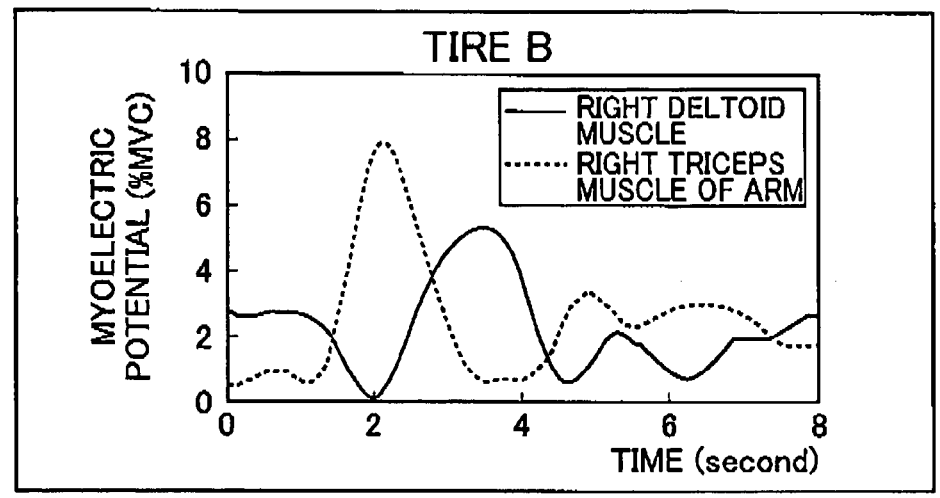
Figure 18C:
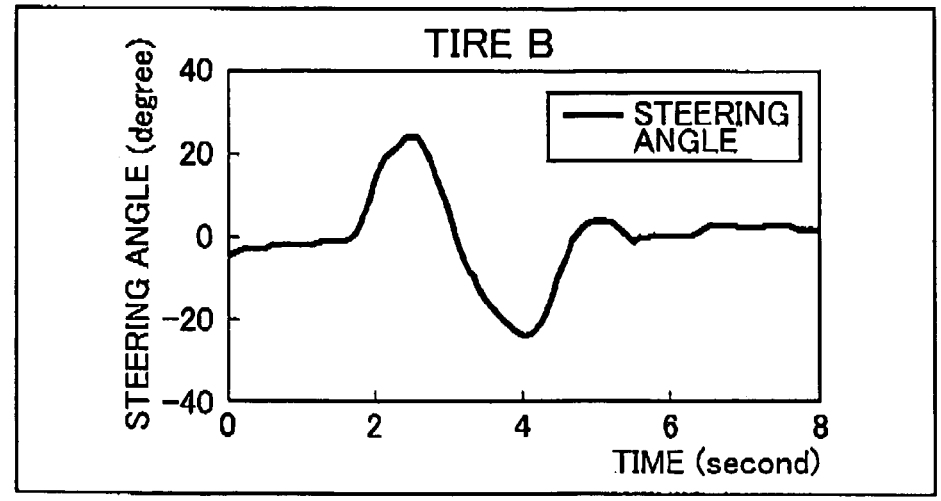
Figure 19A:
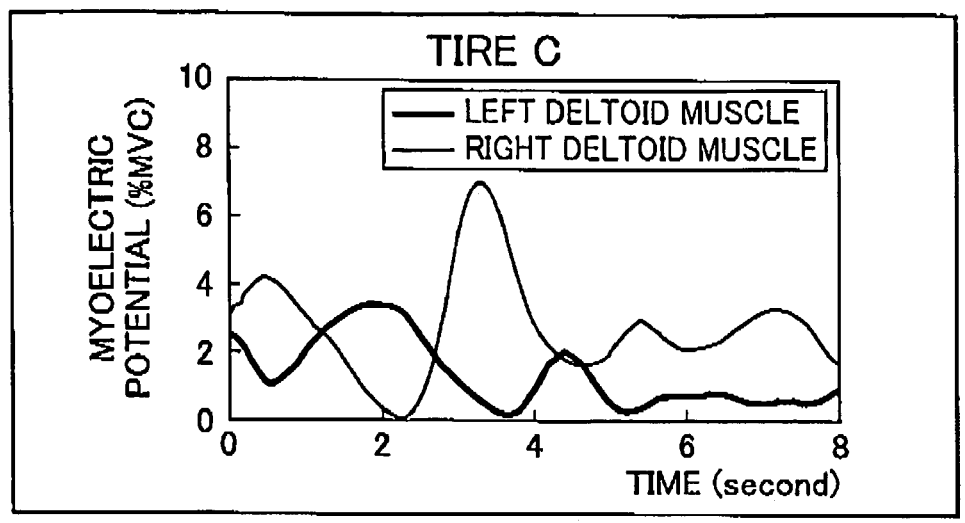
FIGS. 19A to 19C are graphs showing respective measured waveforms of a steering angle and myoelectric potentials when a vehicle equipped with tires C was driven.
Figure 19B:
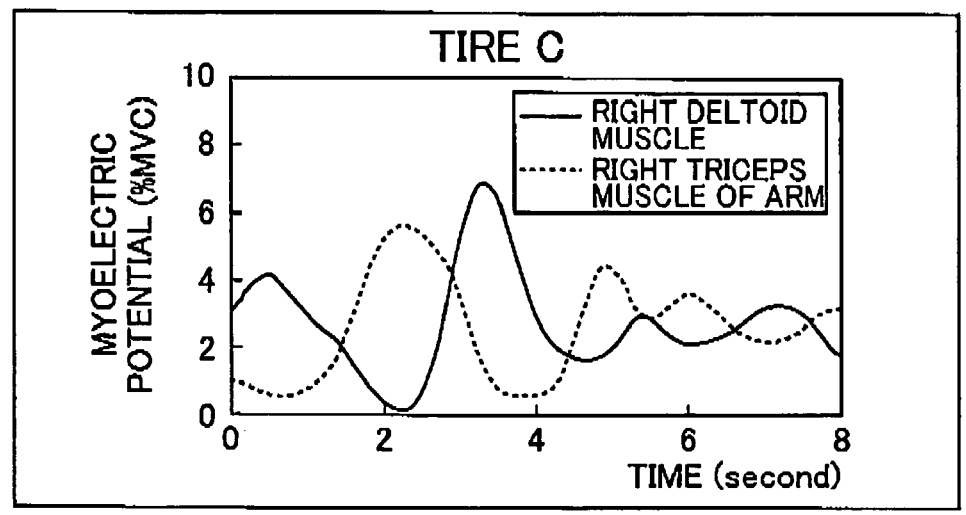
Figure 19C:
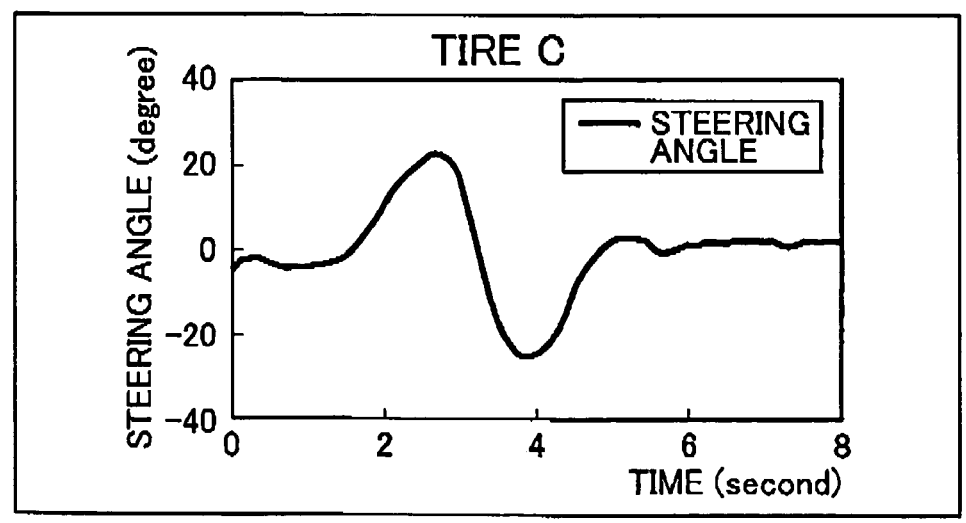

FIGS. 17A to 17C show values measured when the vehicle equipped with the tires A was driven. FIGS. 18A to 18C show values measured when the vehicle equipped with the tires B was driven. FIGS. 19A to 19C show values measured when the vehicle equipped with the tires C was driven.

Figure 20A:
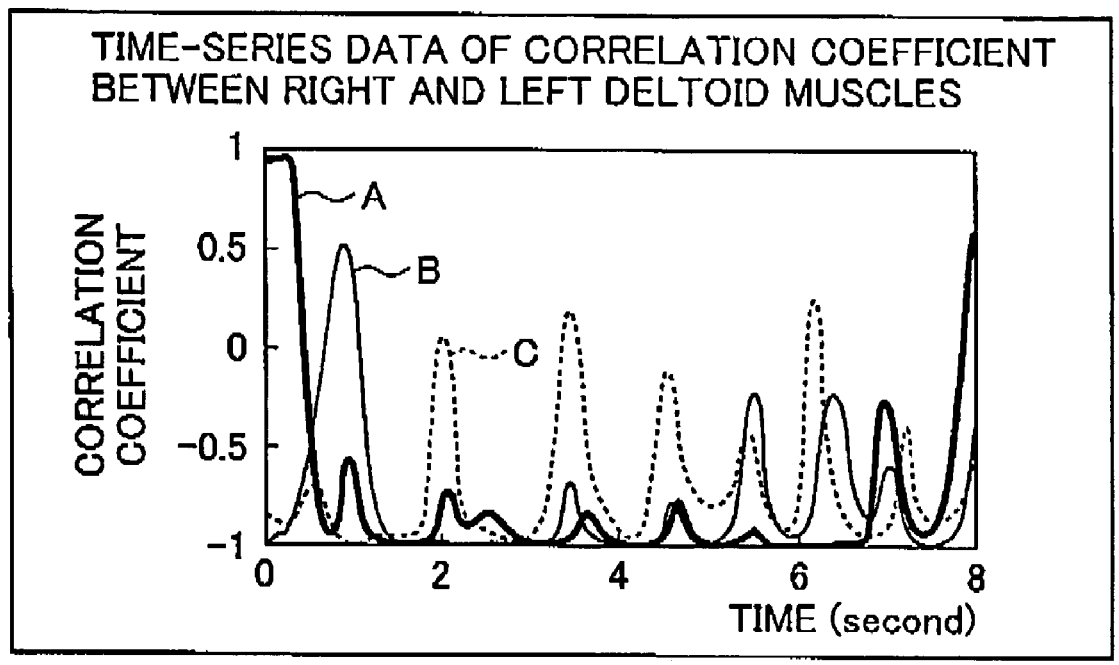
FIGS. 20A and 20B are graphs showing time-series data of the first correlation coefficients associated with two pairs of antagonistic muscles.
Figure 20B:
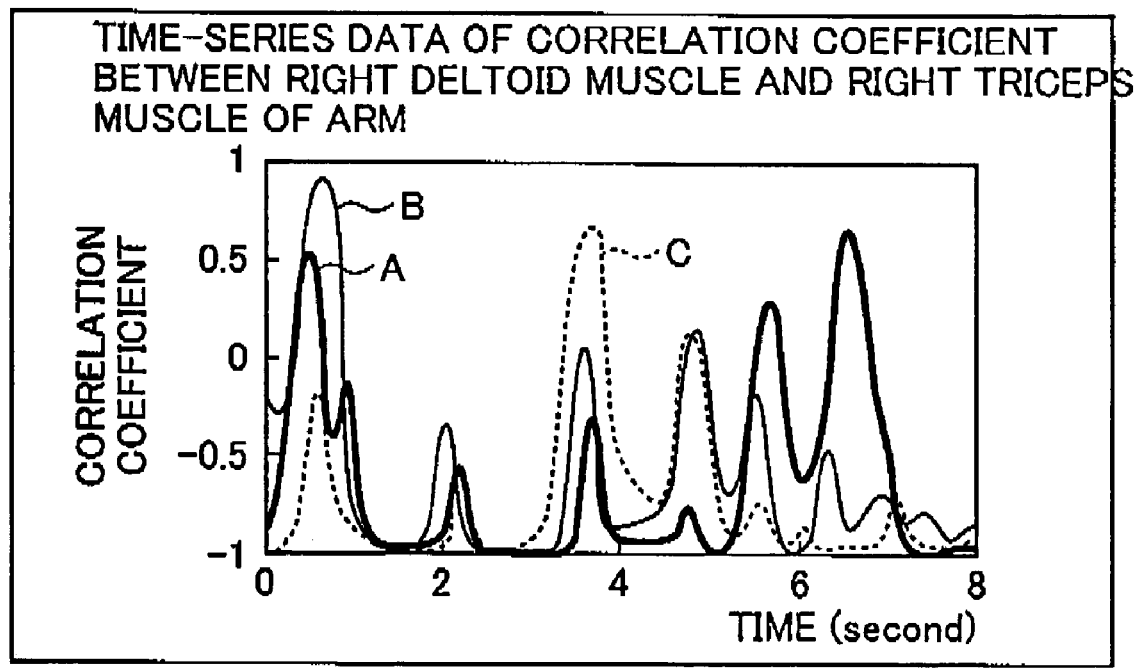

FIGS. 20A and 20B show two time-series data of first correlation coefficients associated with myoelectric potential signals from two pairs of antagonistic muscles when the vehicles equipped with the tires A, B, and C were driven. FIG. 20A shows the time-series data of the first correlation coefficient obtained from the left and right deltoid muscles and FIG. 20B shows the time-series data of the first correlation coefficient obtained from the right deltoid muscle and the right triceps muscle.

Figure 21:
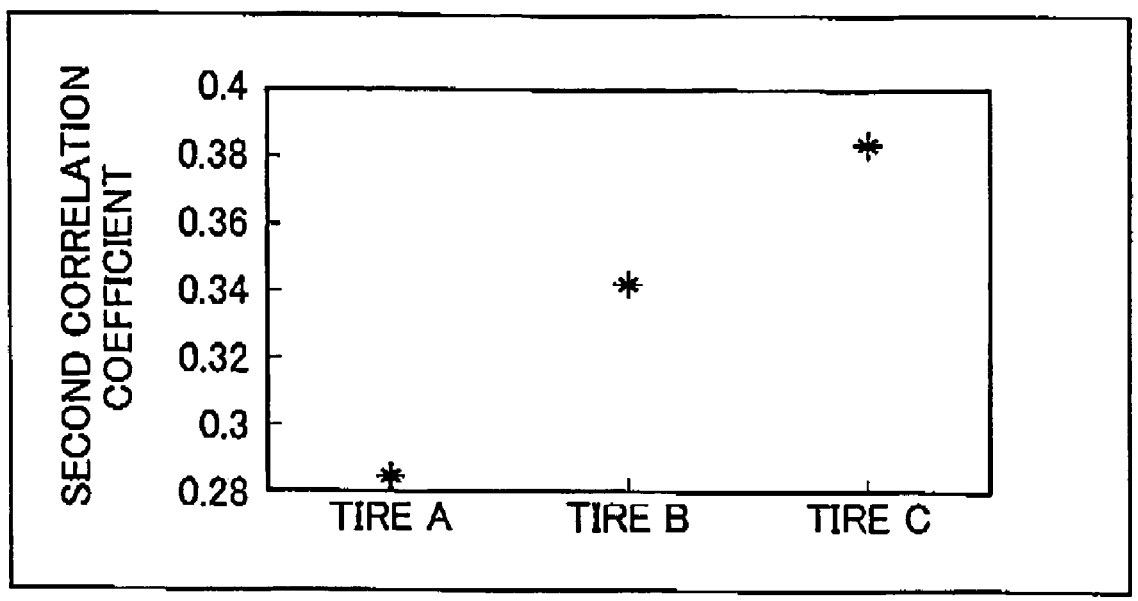
FIG. 21 is a graph showing the second correlation coefficient between the time-series data of the first correlation coefficients shown in FIGS. 20A and 20B.

FIG. 21 shows a second correlation coefficient between the time-series data of the first correlation coefficient obtained from the left and right deltoid muscles and the time-series data of the first correlation coefficient obtained from the right deltoid muscle and the right triceps muscle.

As can be understood from FIG. 21, the operability of the tire A is highest, the operability of the tire B is the second highest, and the operability of the tire C is the lowest.

Then, the subject under measurement made actual subjective evaluations, so that the reliability of the smoothness evaluation of the operations based on the myoelectric potential signals using the time-series data of the first correlation coefficients was examined.

The subjective evaluations pertain to grip feeling which is felt by the subject under measurement when he or she drove the vehicles equipped with the three types of test tires (A, B, and C). The results of the subjective evaluations are shown in Table 5. The subjective evaluations were performed on a 1-to-5 scale, adding a plus (+) sign or a minus (−) sign to each evaluation rating, as needed.

TABLE 5

|  | Tire A | Tire B | Tire C |
| --- | --- | --- | --- |
| Line Tracing Performance | 3+ | 3 | 2.5− |

As can be understood from the results of Table 5, the line tracing performance of the tire A is the highest, the line tracing performance of the tire B is the second highest, and the line tracing performance of the tire C is the lowest. The results of the subjective evaluations coincide with the results of the evaluations using the time-series data of the first correlation coefficients shown in FIG. 21.

From the foregoing, it will be understood that the smoothness evaluation of an operation based on myoelectric potential signals using time-series data of the first correlation coefficients is substantially the same as a subjective evaluation based on the perception of the subject under measurement. Hence, the smoothness of an operation can be evaluated quantitatively by using myoelectric potentials.

The workability evaluating apparatus according to the present invention has been described in detail, and the present invention is not limited to the embodiments described above. Various changes and modifications can be made to the invention without departing from the gist thereof.

What is claimed is:

1. A workability evaluating apparatus, comprising:
   a myoelectric potential detecting unit for detecting time-series fluctuations in myoelectric potentials of at least one pair of antagonistic muscles, which show antagonistic activities while operating equipment among muscles of an operator used to operate the equipment, as myoelectric potential signals;
   a signal processing unit for processing the detected myoelectric potentials to obtain processed myoelectric potential signals of respective antagonistic muscles in said at least one pair of antagonistic muscles;
   an arithmetic operation unit for calculating time-series data of a first correlation coefficient in a specified sampling time by calculating said first correlation coefficient between two signal values at each time in said processed myoelectric potential signals obtained by processing the myoelectric potential signals from the at least one pair of antagonistic muscles, and for performing evaluation of workability in operating the equipment by using values of the calculated time-series data of the first correlation coefficient, wherein the workability is an index for indicating operability when the operator operates the equipment; and
   an output unit for outputting a result of the evaluation performed by said arithmetic operation unit.

2. The workability evaluating apparatus according to claim 1, wherein:
   said arithmetic operation unit calculates plural time-series data of the first correlation coefficients associated with myoelectric potential signals from two or more pairs of antagonistic muscles detected by said myoelectric potential detecting unit, and evaluates the workability in operating the equipment by using the plural time-series data of two or more first correlation coefficients obtained from the individual pairs of antagonistic muscles.

3. The workability evaluating apparatus according to claim 2, wherein the myoelectric potential signals detected by said myoelectric potential detecting unit comprise myoelectric potential signals from a pair of left and right antagonistic muscles in the operator and myoelectric potential signals from a pair of antagonistic muscles in one of a right and a left part of a body of the operator.

4. The workability evaluating apparatus according to claim 3, wherein:
   said arithmetic operation unit calculates a second correlation coefficient between time-series data of the first correlation coefficient between the myoelectric potential signals from the pair of left and right antagonistic muscles in the operator and time-series data of the first correlation coefficient between the myoelectric potential signals from the pair of antagonistic muscles in one of the right and the left part of the body of the operator, and evaluates the workability in operating the equipment based on the second correlation coefficient between the plural time-series data.

5. The workability evaluating apparatus according to claim 1, further comprising:
   an operation-input-quantity detecting unit for detecting an input quantity imparted to an operated portion of the operated equipment; and
   an operational displacement processing unit for calculating a basic period of the operation from time-series data of the detected input quantity and determining the length of the sampling time based on the basic period, wherein the determined sampling time is used for calculating the time-series data of the first correlation coefficient by said arithmetic operation unit.

6. The workability evaluating apparatus according to claim 5, wherein the sampling time ranges from 25% to 100% of the basic period.

7. The workability evaluating apparatus according to claim 5, wherein the input quantity is one of a quantity of displacement of the operated portion and a quantity of angular displacement thereof.

8. The workability evaluating apparatus according to claim 5, wherein the input quantity is one of a force and a torque that act on the operated portion.

9. The workability evaluating apparatus according to claim 1, wherein said signal processing unit rectifies and smoothes said detected myoelectric potential signals by said myoelectric potential detecting unit to obtain said processed myoelectric potential signals of respective antagonistic muscles in said at least one pair of antagonistic muscles.

10. The workability evaluating apparatus according to claim 1, wherein said signal processing unit performs full-wave rectification on said detected myoelectric potential signals by said myoelectric potential detecting unit, and performs a smoothing process on said rectified myoelectric potentials by moving average, low pass filtering or band pass filtering to obtain said processed myoelectric potential signals of respective antagonistic muscles in said at least one pair of antagonistic muscles.

11. The workability evaluating apparatus according to claim 1, wherein:
   said values of said time-series data of said first correlation coefficient calculated by said arithmetic operation unit range from −1 to +1; and
   said arithmetic operation unit evaluates said workability in operating said equipment as having excellent smoothness in operating said equipment when said values of said time-series data of said first correlation coefficient are negative or approach −1, and as not having excellent smoothness in operating said equipment when said values of said time-series data of said first correlation coefficient are positive or approach +1.

12. The workability evaluating apparatus according to claim 1, wherein:

said values of said time-series data of said first correlation coefficient calculated by said arithmetic operation unit range from −1 to +1; and said arithmetic operation unit evaluates said workability in operating said equipment as having negative correlation or strong negative correlation between two signal values in said processed myoelectric potential signals from the at least one pair of antagonistic muscles and excellent operability in operating said equipment when said values of said time-series data of said first correlation coefficient are negative or approach −1, and as having positive correlation or strong positive correlation between two signal values in said processed myoelectric potential signals from the at least one pair of antagonistic muscles and not having excellent operability in operating said equipment when said values of said time-series data of said first correlation coefficient are positive or approach +1.

* * * * *